(12) United States Patent
Reiner

(10) Patent No.: US 8,412,544 B2
(45) Date of Patent: Apr. 2, 2013

(54) METHOD AND APPARATUS OF DETERMINING A RADIATION DOSE QUALITY INDEX IN MEDICAL IMAGING

(76) Inventor: Bruce Reiner, Berlin, MD (US)

( * ) Notice: Subject to any disclaimer, the term of this patent is extended or adjusted under 35 U.S.C. 154(b) by 0 days.

(21) Appl. No.: 13/064,522

(22) Filed: Mar. 30, 2011

(65) Prior Publication Data

US 2011/0270623 A1    Nov. 3, 2011

Related U.S. Application Data

(63) Continuation-in-part of application No. 11/976,518, filed on Oct. 25, 2007.

(60) Provisional application No. 61/282,770, filed on Mar. 30, 2010.

(51) Int. Cl.
*G06Q 50/00* (2012.01)
(52) U.S. Cl. ............... 705/3; 705/2; 600/300; 348/62
(58) Field of Classification Search .......... 705/2–3; 600/300; 348/62
See application file for complete search history.

(56) References Cited

U.S. PATENT DOCUMENTS

| | | | |
|---|---|---|---|
| 4,260,894 A * | 4/1981 | Neumann | 378/16 |
| 5,173,609 A | 12/1992 | Lacoste et al. | |
| 5,511,549 A | 4/1996 | Legg et al. | |
| 5,513,101 A | 4/1996 | Pinsky et al. | |
| 5,621,779 A | 4/1997 | Hughes et al. | |
| 5,655,084 A | 8/1997 | Pinsky et al. | |
| 5,673,332 A * | 9/1997 | Nishikawa et al. | 382/128 |
| 5,844,241 A * | 12/1998 | Liu et al. | 250/363.04 |
| 5,905,262 A * | 5/1999 | Spanswick | 250/368 |
| 6,058,322 A | 5/2000 | Nishikawa et al. | |
| 6,200,025 B1 | 3/2001 | Rich | |
| 6,222,544 B1 | 4/2001 | Tarr et al. | |
| 6,373,972 B1 | 4/2002 | Nonomura | |
| 6,422,751 B1 * | 7/2002 | Aufrichtig et al. | 378/207 |
| 6,463,181 B2 | 10/2002 | Duarte | |
| 6,487,513 B1 | 11/2002 | Eastvold et al. | |
| 6,628,201 B2 | 9/2003 | Cho et al. | |
| 6,717,154 B2 | 4/2004 | Black et al. | |
| 6,728,662 B2 | 4/2004 | Frost et al. | |
| 6,785,410 B2 | 8/2004 | Vining et al. | |
| 6,790,178 B1 | 9/2004 | Mault et al. | |
| 6,891,476 B2 | 5/2005 | Kitaguchi et al. | |
| 6,919,556 B1 | 7/2005 | Laurence | |
| 7,065,235 B2 * | 6/2006 | Dewaele | 382/132 |
| 7,084,410 B2 | 8/2006 | Beloussov et al. | |
| 7,171,252 B1 | 1/2007 | Scarantino et al. | |
| 7,205,544 B2 | 4/2007 | Bushberg | |

(Continued)

OTHER PUBLICATIONS

Donnelly, Lane F., et al. "Minimizing Radiation Dose for Pediatric Body Applications of Single-Detector Helical CT", Aug. 2, 2000, American Journal of Roetgenology, 1-13.

*Primary Examiner* — Sind Phongsvirajati
(74) *Attorney, Agent, or Firm* — Jean C. Edwards, Esq.; Edwards Neils PLLC

(57) ABSTRACT

The present invention relates to a method and apparatus which quantifies radiation safety in medical imaging through the creation and analysis of objective data for each individual imaging procedure with respect to acquisition parameters, calculated radiation dose, and clinical data related to imaging examination selection and performance. The present invention also calculates a cumulative radiation dose based upon an individual patient's entire medical record, along with occupational and environmental exposures, to calculate a dynamic cumulative radiation-induced carcinogenesis risk. The present invention provides reforms to improve patient safety, quality and accountability, by creating a technology which simultaneously records and tracks objective data referable to radiation safety, medical imaging quality, and accountability among the various stakeholders and technologies in use. This quantifiable data is referred to as the Radiation Dose Quality Index (RDQI), and creates an objective, data-driven measure of quality and safety as it relates to medical practice.

38 Claims, 5 Drawing Sheets

U.S. PATENT DOCUMENTS

| | | | |
|---|---|---|---|
| 7,206,789 B2 | 4/2007 | Hurmiz et al. | |
| 7,254,643 B1 | 8/2007 | Peters, Jr. et al. | |
| 7,261,690 B2 | 8/2007 | Teller et al. | |
| 7,272,530 B2 | 9/2007 | Hsiung et al. | |
| 2001/0038681 A1* | 11/2001 | Stanton et al. | 378/55 |
| 2002/0027973 A1* | 3/2002 | Spaak | 378/95 |
| 2002/0131552 A1* | 9/2002 | Nishizawa et al. | 378/65 |
| 2003/0074228 A1 | 4/2003 | Walsh | |
| 2005/0027196 A1* | 2/2005 | Fitzgerald | 600/436 |
| 2005/0111621 A1* | 5/2005 | Riker et al. | 378/65 |
| 2005/0203775 A1* | 9/2005 | Chesbrough | 705/2 |
| 2005/0209888 A1 | 9/2005 | Oowaki et al. | |
| 2005/0256743 A1* | 11/2005 | Dale | 705/2 |
| 2006/0017009 A1 | 1/2006 | Rink et al. | |
| 2006/0085223 A1 | 4/2006 | Anderson et al. | |
| 2006/0274145 A1* | 12/2006 | Reiner | 348/62 |
| 2007/0162311 A1 | 7/2007 | Gentles | |

* cited by examiner

METHOD AND APPARATUS OF DETERMINING A RADIATION DOSE QUALITY INDEX IN MEDICAL IMAGING

CROSS-REFERENCE TO RELATED APPLICATIONS

The present application claims priority from U.S. Provisional Patent Application No. 61/282,770 filed Mar. 30, 2010, and is a continuation-in-part of pending U.S. patent application Ser. No. 11/976,518, filed Oct. 25, 2007, the contents of both of which are herein incorporated by reference in their entirety.

BACKGROUND OF THE INVENTION

One of the long recognized perils of medical imaging is the use of ionizing radiation, which has been shown to be associated with carcinogenesis. A number of diagnostic medical imaging modalities and applications utilize ionizing radiation including radiography, mammography, computed tomography (CT), nuclear medicine, and other forms of molecular imaging. In addition, therapeutic radiology utilizes ionizing radiation for treatment in patients with various forms of cancer. Collectively, these diagnostic and therapeutic medical applications pose significant iatrogenic risk to the patient, and must be justified through risk-benefit analysis to substantiate the medical efficacy of use.

Thus, while radiation safety and medical imaging quality are often viewed in isolation, the reality is that they are often directly related to one another. A given medical imaging procedure (e.g., abdominal CT examination) is associated with a quantifiable amount of ionizing radiation, which is dependent upon the acquisition parameters selected, the technology utilized, and various attributes of the patient on which the examination is being performed. If one were to attempt to adjust the acquisition parameters in an attempt to reduce radiation dose, a concomitant effect would take place on overall image quality, largely due to increased noise. As a result, attempts to modify radiation dose (to improve radiation safety) without determining the resultant impact on image quality are somewhat misguided. Radiation dose and image quality are inextricably related to one another and as a result should always be considered in combination.

A number of recent medical, political, and societal initiatives are underway to analyze the use of ionizing radiation in medicine. While these initiatives are arguably long overdue, minimal technology development and few industry-wide standards are in place to provide the requisite infrastructure to maximize the likelihood of success. In particular, long-term success requires a mechanism to prospectively record and analyze individual and cumulative radiation dose exposures associated with medical practice.

While these efforts are underway for creation of radiation standards in medicine, parallel efforts are being made to objectively quantify and analyze quality within medical imaging. The overarching theme in such an endeavor is that improved quality ultimately translates into improved clinical outcomes. The parallel efforts aimed at improving radiation safety and quality in medicine have been encouraged and accelerated by a number of high profile publications issued by the Institute of Medicine, which has cited the unusually high number of errors in medical practice resulting in excessive morbidity and mortality. These publications have called for sweeping reforms in medicine aimed at improving patient safety, quality, and accountability.

Accordingly, a method and apparatus for quantifying radiation safety in medical imaging is needed, where objective data is created for each individual imaging procedure related to acquisition parameters, radiation dose, and clinical data related to exam selection and performance. Further, a method and apparatus to calculate cumulative radiation dose based upon an individual patient's entire medical record, along with occupational and environmental exposures, to calculate a dynamic cumulative radiation-induced carcinogenesis risk, is also required.

SUMMARY OF THE INVENTION

The present invention relates to a method and apparatus which quantifies radiation safety in medical imaging through the creation and analysis of objective data for each individual imaging procedure with respect to acquisition parameters, calculated radiation dose, and clinical data related to imaging examination selection and performance. The present invention also provides a method and apparatus to calculate cumulative radiation dose based upon an individual patient's entire medical record, along with occupational and environmental exposures, to calculate a dynamic cumulative radiation-induced carcinogenesis risk.

The technology associated with the objectification of quality in medical imaging has been described in co-pending U.S. patent application Ser. No. 11/412,884, filed Apr. 28, 2006, and U.S. patent application Ser. No. 12/453,268, filed May 5, 2009, the contents of which are herein incorporated by reference in their entirety. In addition, U.S. Pat. No. 7,532,942, issued May 12, 2009, U.S. Pat. No. 7,831,445, issued Nov. 9, 2010, U.S. Pat. No. 7,853,476, issued Dec. 14, 2010, U.S. patent application Ser. No. 11/699,344, filed Jan. 30, 2007, and U.S. patent application Ser. No. 12/213,184, filed Jun. 16, 2008, the contents of all of which are herein incorporated by reference in their entirety, provide the technological infrastructure to record, track, analyze, and cross-reference objective quality metrics in medical imaging, while serving as a source for automated decision support and establishment of data-driven best practice guidelines, which is the theme behind Evidence-Based Medicine.

Thus, the present invention relates to a method and apparatus to accomplish the goal of providing reforms to improve patient safety, quality and accountability, by creating a technology which simultaneously records and tracks objective data referable to radiation safety, medical imaging quality, and accountability among the various stakeholders and technologies in use. This quantifiable data is referred to as the Radiation Dose Quality Index (RDQI), and creates an objective, data-driven measure of quality and safety as it relates to medical practice.

In one embodiment, the present invention contains several different components which can be used on an individual or collective basis, including 1) a radiation dose calculator, 2) objective quality assessment tool, 3) an individual and collective database(s) (Radiation, Quality, Clinical), 4) decision support features, 5) supporting technologies, and 6) outcomes analysis, which provide an objective and quantifiable metric for correlating the variables of radiation dose and image quality.

In one embodiment, the program retrieves and displays the patient's prior clinical, laboratory, and imaging data from the various databases, for clinical review. Included in the imaging data are a series of examination and patient-specific data related to individual exam radiation dose, cumulative radiation dose, and radiation iatrogenic risk. The program provides several analytics to the user, including the carcinogenesis risk associated with prior imaging studies, along with estimated environmental radiation exposures. Other iatrogenic risks of radiation (distinct from carcinogenesis) may be compiled by the program. In addition, the program provides additional comparative data, to assist the user in the examination selection and ordering process.

In one embodiment, a decision support application is presented by the program, and the program retrieves and displays additional information regarding the report findings and radiation data attributable to the prior imaging studies. This data can be exported electronically from the outside institutional database to the in-house database by activating an electronic transfer function. The program provides data on individual exam radiation dose exposures, cumulative patient radiation dose exposure, estimated environmental radiation dose exposure, radiation-induced carcinogenesis risk, cumulative carcinogenesis risk (taking into account all patient-specific cancer risk factors), and additional radiation risk (i.e., for non-carcinogenic disease). In the determination of the imaging examination and protocol selection, the program derives the estimated radiation dose exposures, estimated cost estimates, comparative clinical value, options for radiation dose reduction, options for enhancing clinical value, options for minimizing cost, and comprehensive cost-benefit analysis.

In one embodiment, the program provides a detailed analysis to assist in the exam selection process. When the user selects an option, for data on, for example, the estimated dose for conventional CT, an estimated dose for low dose, and estimated dose for ultra-low dose CT, are provided. After selecting one option, the program may provide the decision support option of "protocol optimization". The program processes the clinical, imaging, and historical data to create the optimal CT protocol to maximize radiation dose reduction, enhance image quality, and provide accurate diagnostic accuracy. The protocol optimization schema would include acquisition parameters, CT kernel, collimation, image processing, and noise reduction filters.

In one embodiment, the protocol optimization schema can be performed by the program using several options, such as institutional-specific protocol optimization, regional protocol optimization, or an all institutions protocol optimization.

In one embodiment, the examination order entry process is inputted into the computer system, and after completion of the order entry process, the examination is scheduled. At the examination, the patient and technologist performing the examination can undergo authentication by the program of their credentials locally (using Biometrics), and the patient information is then retrieved by the program from the corresponding databases.

In one embodiment, the ordering information and decision support recommendations are displayed by the program, and are reviewed by the technologist. In one embodiment, optimal acquisition parameters using the JND metric protocol may be requested.

In one embodiment, the JND metric protocol includes having the technologist acquire a "test" CT image, in the region of interest, using standard "default" CT acquisition parameters, determined by the quality assessment tool using the image quality databases. Computer-derived noise is introduced by the program into this test image, in order to mimic the CT appearance using low dose acquisition parameters. The amount of introduced noise is progressively increased by the program until a pre-determined minimal quality threshold (MQT) is reached.

In one embodiment, the MQT score is determined by the program based upon the clinical parameters, patient profile, examination being performed, technology utilized, and individual radiologist profile. The MQT score may be determined to be the equivalent of 1 JND (just noticeable difference).

In one embodiment, the perceptual and program-derived image quality are determined by the program, and then the computer derived 1 JND image is reviewed to ensure that the perceptual and computer-derived image quality are satisfactory. Then, the acquisition parameters are calculated by the program, which will produce the desired CT image quality (1 JND); and if necessary, imaging quality requirements can be dynamically adjusted by the program. This process may be repeated at multiple levels within the anatomic region of interest, in order to dynamically optimize acquisition parameters at multiple levels of strategic importance.

In one embodiment, after a full study of the patient is acquired according to the examination order, a comprehensive exam radiation dose (Radiation Scorecard) is calculated by the program, and recorded in the RDQI database. This value can be compared by the program against the computer derived "standard" radiation dose, which is calculated by the program based upon standard "default" CT acquisition parameters. An additional exam-specific radiation dose quality index (RDQI) is recorded by the program, which reflects the total examination radiation dose and the objective measure of image quality.

In one embodiment, the technologist applies specialized noise reduction filters and/or image processing algorithms to the "raw" imaging dataset in order to decrease noise and enhance contrast resolution. The completed CT image dataset is then transferred by the program to the PACS for radiologist interpretation. Interpretation of the imaging dataset is performed by a radiologist, where the radiologist determines the optimal manner in which the imaging data is processed, reconstructed, displayed, and analyzed, by the program.

In one embodiment, a number of different forms of computerized decision support can be applied by the program, to assist the radiologist in analysis of the imaging dataset. One form of decision support is computer-aided detection (CAD) software, which is specifically designed to detect a specific type of pathology. Another computerized decision support application can analyze morphology and/or texture of the tissue, and provide probability statistics as to suspected clinical significance (i.e., probability of malignancy). The relative performance of these computerized CAD programs are dependent upon the acquisition parameters of the imaging dataset, which have been customized to minimize radiation dose at the pre-defined quality threshold (MQT). Thus, the CAD program selection may be tailored to the acquisition parameters employed.

In one embodiment, a number of technical resources can be utilized by the program to enhance radiologist performance (e.g., image processing, CAD), but the RDQI program still accurately records, tracks, and analyzes potential differences in radiologist performance, and utilizes this data proactively to maximize clinical outcomes.

In one embodiment, the overall process and analysis of RDQI is administrative oversight, is important in ensuring that departmental performance standards are being maintained (relative to technology and staff performance), that there is ongoing education and training efforts aimed at improving deficiencies, and there is compliance with industry and governmental regulations. The various administrative analyses which can be performed using the RDQI program include: mean radiation dose according to exam type, mean quality scores according to exam type, and mean MQT Scores. As stated above, the administrative analyses can be performed and tracked by the program according to modality, anatomy, clinical indication, and technology utilized.

In one embodiment, in addition to administrative analysis, the RDQI plays a major role in comparative technology assessment, to effectively use the program to compare different technology providers, after accounting for institutional, staff, and patient differences. The program can quantitatively compare mean exam radiation dose, mean quality, and MQT scores. A prospective customer could make an informed and educated decision as to the most cost effective technology to purchase, after review by the program and factoring in its own institutional, patient, and staff variables. At the same time, a digital mammography vendor can utilize the program to accurately compare radiation and quality data of its customers, to determine the net effect the new and old detector technologies had on technical and clinical performance.

In one embodiment a therapeutic RDQI database provides an objective way to assess technology and individual stakeholder performance in the radiation therapy; taking into account a number of clinical and technical variables. The clinical outcomes can be determined by the program.

In one embodiment, there are at least three components of the invention, all of which are contained within the RDQI database, including the "Technical" component, which defines an objective and quantifiable relationship between radiation safety (as determined by radiation dose) and image quality; the "Professional" RDQI analysis, which correlates radiation safety, image quality, and interpretation accuracy data; and the "Therapeutic" RDQI analysis, which defines the relationship between radiation dose and quality relating to therapeutic applications of radiology (e.g., radiation oncology). The "technical", "professional", and "therapeutic" RDQI analytics can be used to determine best clinical practice guidelines, technology selection, and relative performance differentiation of different service providers.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

Figure 1:
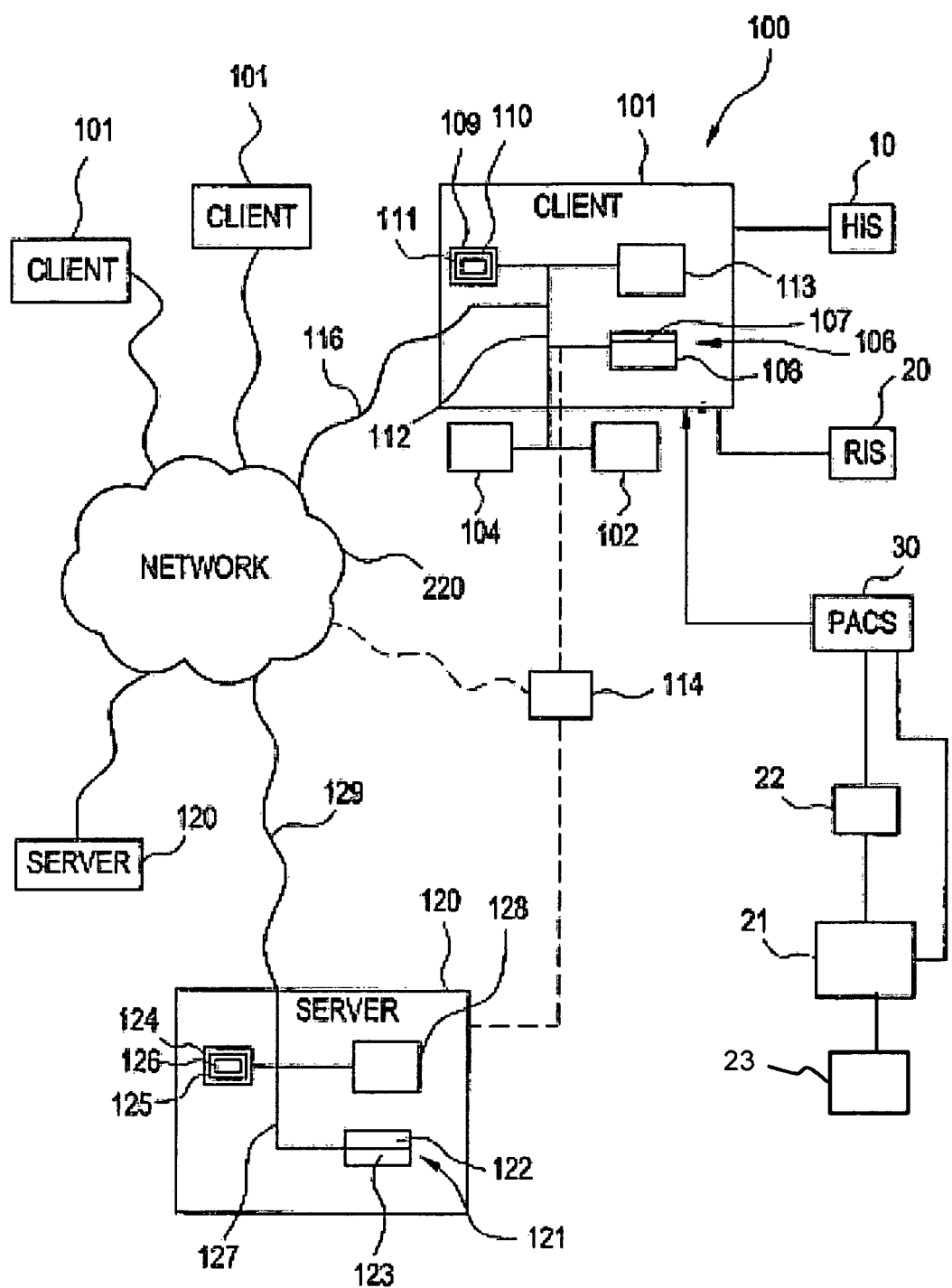
FIG. 1 is a schematic diagram of a system for quantifying radiation safety in medical imaging, according to one embodiment consistent with the present invention.

According to one embodiment of the invention illustrated in FIG. 1, medical (radiological) applications may be implemented using the system 100. The system 100 is designed to interface with existing information systems such as a Hospital Information System (HIS) 10, a Radiology Information System (RIS) 20, an acquisition or radiographic device 21, and/or other information systems that may access a computed radiography (CR) cassette or direct radiography (DR) system, a CR/DR plate reader 22, a Picture Archiving and Communication System (PACS) 30, and/or other systems, such as a Quality Assurance (QA) Sensor 23, which is connected to the patient to record certain metrics. The system 100 may be designed to conform with the relevant standards, such as the Digital Imaging and Communications in Medicine (DICOM) standard, DICOM Structured Reporting (SR) standard, and/or the Radiological Society of North America's Integrating the Healthcare Enterprise (IHE) initiative, among other standards.

According to one embodiment, bi-directional communication between the system 100 of the present invention and the information systems, such as the HIS 10, RIS 20, QA sensor device 21, CR/DR plate reader 22, and PACS 30, etc., may be enabled to allow the system 100 to retrieve, and/or provide information from/to these systems. According to one embodiment of the invention, bi-directional communication between the system 100 of the present invention and the information systems allows the system 100 to update information that is stored on the information systems. According to one embodiment of the invention, bi-directional communication between the system 100 of the present invention and the information systems allows the system 100 to generate desired reports and/or other information.

The system 100 of the present invention includes a client computer 101, such as a personal computer (PC), which may or may not be interfaced or integrated with the PACS 30. The client computer 101 may include an imaging display device 102 that is capable of providing high resolution digital images in 2-D or 3-D, for example. According to one embodiment of the invention, the client computer 101 may be a mobile terminal if the image resolution is sufficiently high. Mobile terminals may include mobile computing devices, a mobile data organizer (PDA), or other mobile terminals that are operated by the user accessing the program 110 remotely.

According to one embodiment of the invention, an input device 104 or other selection device, may be provided to select hot clickable icons, selection buttons, and/or other selectors that may be displayed in a user interface using a menu, a dialog box, a roll-down window, or other user interface. The user interface may be displayed on the client computer 101. According to one embodiment of the invention, users may input commands to a user interface through a programmable stylus, keyboard, mouse, speech processing device, laser pointer, touch screen, or other input device 104.

According to one embodiment of the invention, the input or other selection device 104 may be implemented by a dedicated piece of hardware or its functions may be executed by code instructions that are executed on the client processor 106. For example, the input or other selection device 104 may be implemented using the imaging display device 102 to display the selection window with a stylus or keyboard for entering a selection.

According to another embodiment of the invention, symbols and/or icons may be entered and/or selected using an input device 104, such as a multi-functional programmable stylus. The multi-functional programmable stylus may be used to draw symbols onto the image and may be used to accomplish other tasks that are intrinsic to the image display, navigation, interpretation, and reporting processes, as described in U.S. patent application Ser. No. 11/512,199 filed on Aug. 30, 2006, the entire contents of which are hereby incorporated by reference. The multi-functional programmable stylus may provide superior functionality compared to traditional computer keyboard or mouse input devices. According to one embodiment of the invention, the multi-functional programmable stylus also may provide superior functionality within the PACS and Electronic Medical Report (EMR).

According to one embodiment of the invention, the client computer 101 may include a processor 106 that provides client data processing. According to one embodiment of the invention, the processor 106 may include a central processing unit (CPU) 107, a parallel processor, an input/output (I/O) interface 108, a memory 109 with a program 110 having a data structure 111, and/or other components. According to one embodiment of the invention, the components all may be connected by a bus 112. Further, the client computer 101 may include the input device 104, the image display device 102, and one or more secondary storage devices 113. According to one embodiment of the invention, the bus 112 may be internal to the client computer 101 and may include an adapter that enables interfacing with a keyboard or other input device 104. Alternatively, the bus 112 may be located external to the client computer 101.

According to one embodiment of the invention, the image display device 102 may be a high resolution touch screen computer monitor. According to one embodiment of the invention, the image display device 102 may clearly, easily and accurately display images, such as x-rays, and/or other images. Alternatively, the image display device 102 may be implemented using other touch sensitive devices including tablet personal computers, pocket personal computers, plasma screens, among other touch sensitive devices. The touch sensitive devices may include a pressure sensitive screen that is responsive to input from the input device 104, such as a stylus, that may be used to write/draw directly onto the image display device 102.

According to another embodiment of the invention, high resolution goggles may be used as a graphical display to provide end users with the ability to review images. According to another embodiment of the invention, the high resolution goggles may provide graphical display without imposing physical constraints of an external computer.

According to another embodiment, the invention may be implemented by an application that resides on the client computer 101, wherein the client application may be written to run on existing computer operating systems. Users may interact with the application through a graphical user interface. The client application may be ported to other personal computer (PC) software, personal digital assistants (PDAs), cell phones, and/or any other digital device that includes a graphical user interface and appropriate storage capability.

According to one embodiment of the invention, the processor 106 may be internal or external to the client computer 101. According to one embodiment of the invention, the processor 106 may execute a program 110 that is configured to perform predetermined operations. According to one embodiment of the invention, the processor 106 may access the memory 109 in which may be stored at least one sequence of code instructions that may include the program 110 and the data structure 111 for performing predetermined operations. The memory 109 and the program 110 may be located within the client computer 101 or external thereto.

While the system of the present invention may be described as performing certain functions, one of ordinary skill in the art will readily understand that the program 110 may perform the function rather than the entity of the system itself.

According to one embodiment of the invention, the program 110 that runs the system 100 may include separate programs 110 having code that performs desired operations. According to one embodiment of the invention, the program 110 that runs the system 100 may include a plurality of modules that perform sub-operations of an operation, or may be part of a single module of a larger program 110 that provides the operation.

According to one embodiment of the invention, the processor 106 may be adapted to access and/or execute a plurality of programs 110 that correspond to a plurality of operations. Operations rendered by the program 110 may include, for example, supporting the user interface, providing communication capabilities, performing data mining functions, performing e-mail operations, and/or performing other operations.

According to one embodiment of the invention, the data structure 111 may include a plurality of entries. According to one embodiment of the invention, each entry may include at least a first storage area, or header, that stores the databases or libraries of the image files, for example.

According to one embodiment of the invention, the storage device 113 may store at least one data file, such as image files, text files, data files, audio files, video files, among other file types. According to one embodiment of the invention, the data storage device 113 may include a database, such as a centralized database and/or a distributed database that are connected via a network. According to one embodiment of the invention, the databases may be computer searchable databases. According to one embodiment of the invention, the databases may be relational databases. The data storage device 113 may be coupled to the server 120 and/or the client computer 101, either directly or indirectly through a communication network, such as a LAN, WAN, and/or other networks. The data storage device 113 may be an internal storage device. According to one embodiment of the invention, the system 100 may include an external storage device 114. According to one embodiment of the invention, data may be received via a network and directly processed.

According to one embodiment of the invention, the client computer 101 may be coupled to other client computers 101 or servers 120. According to one embodiment of the invention, the client computer 101 may access administration systems, billing systems and/or other systems, via a communication link 116. According to one embodiment of the invention, the communication link 116 may include a wired and/or wireless communication link, a switched circuit communication link, or may include a network of data processing devices such as a LAN, WAN, the Internet, or combinations thereof. According to one embodiment of the invention, the communication link 116 may couple e-mail systems, fax systems, telephone systems, wireless communications systems such as pagers and cell phones, wireless PDA's and other communication systems.

According to one embodiment of the invention, the communication link 116 may be an adapter unit that is capable of executing various communication protocols in order to establish and maintain communication with the server 120, for example. According to one embodiment of the invention, the communication link 116 may be implemented using a specialized piece of hardware or may be implemented using a general CPU that executes instructions from program 110. According to one embodiment of the invention, the communication link 116 may be at least partially included in the processor 106 that executes instructions from program 110.

According to one embodiment of the invention, if the server 120 is provided in a centralized environment, the server 120 may include a processor 121 having a CPU 122 or parallel processor, which may be a server data processing device and an I/O interface 123. Alternatively, a distributed CPU 122 may be provided that includes a plurality of individual processors 121, which may be located on one or more machines. According to one embodiment of the invention, the processor 121 may be a general data processing unit and may include a data processing unit with large resources (i.e., high processing capabilities and a large memory for storing large amounts of data).

According to one embodiment of the invention, the server 120 also may include a memory 124 having a program 125 that includes a data structure 126, wherein the memory 124 and the associated components all may be connected through bus 127. If the server 120 is implemented by a distributed system, the bus 127 or similar connection line may be implemented using external connections. The server processor 121 may have access to a storage device 128 for storing preferably large numbers of programs 110 for providing various operations to the users.

According to one embodiment of the invention, the data structure 126 may include a plurality of entries, wherein the entries include at least a first storage area that stores image files. Alternatively, the data structure 126 may include entries that are associated with other stored information as one of ordinary skill in the art would appreciate.

According to one embodiment of the invention, the server 120 may include a single unit or may include a distributed system having a plurality of servers 120 or data processing units. The server(s) 120 may be shared by multiple users in direct or indirect connection to each other. The server(s) 120 may be coupled to a communication link 129 that is preferably adapted to communicate with a plurality of client computers 101.

According to one embodiment, the present invention may be implemented using software applications that reside in a client and/or server environment. According to another embodiment, the present invention may be implemented using software applications that reside in a distributed system over a computerized network and across a number of client computer systems. Thus, in the present invention, a particular operation may be performed either at the client computer 101, the server 120, or both.

According to one embodiment of the invention, in a client-server environment, at least one client and at least one server are each coupled to a network 220, such as a Local Area Network (LAN), Wide Area Network (WAN), and/or the Internet, over a communication link 116, 129. Further, even though the systems corresponding to the HIS 10, the RIS 20, the radiographic device 21, the CR/DR reader 22, and the PACS 30 (if separate) are shown as directly coupled to the client computer 101, it is known that these systems may be indirectly coupled to the client over a LAN, WAN, the Internet, and/or other network via communication links. According to one embodiment of the invention, users may access the various information sources through secure and/or non-secure internet connectivity. Thus, operations consistent with the present invention may be carried out at the client computer 101, at the server 120, or both. The server 120, if used, may be accessible by the client computer 101 over the Internet, for example, using a browser application or other interface.

According to one embodiment of the invention, the client computer 101 may enable communications via a wireless service connection. The server 120 may include communications with network/security features, via a wireless server, which connects to, for example, voice recognition. According to one embodiment, user interfaces may be provided that support several interfaces including display screens, voice recognition systems, speakers, microphones, input buttons, and/or other interfaces. According to one embodiment of the invention, select functions may be implemented through the client computer 101 by positioning the input device 104 over selected icons. According to another embodiment of the invention, select functions may be implemented through the client computer 101 using a voice recognition system to enable hands-free operation. One of ordinary skill in the art will recognize that other user interfaces may be provided.

According to another embodiment of the invention, the client computer 101 may be a basic system and the server 120 may include all of the components that are necessary to support the software platform. Further, the present client-server system may be arranged such that the client computer 101 may operate independently of the server 120, but the server 120 may be optionally connected. In the former situation, additional modules may be connected to the client computer 101. In another embodiment consistent with the present invention, the client computer 101 and server 120 may be disposed in one system, rather being separated into two systems.

Although the above physical architecture has been described as client-side or server-side components, one of ordinary skill in the art will appreciate that the components of the physical architecture may be located in either client or server, or in a distributed environment.

Further, although the above-described features and processing operations may be realized by dedicated hardware, or may be realized as programs having code instructions that are executed on data processing units, it is further possible that parts of the above sequence of operations may be carried out in hardware, whereas other of the above processing operations may be carried out using software.

The underlying technology allows for replication to various other sites. Each new site may maintain communication with its neighbors so that in the event of a catastrophic failure, one or more servers 120 may continue to keep the applications running, and allow the system to load-balance the application geographically as required.

Further, although aspects of one implementation of the invention are described as being stored in memory, one of ordinary skill in the art will appreciate that all or part of the invention may be stored on or read from other computer-readable media, such as secondary storage devices, like hard disks, floppy disks, CD-ROM, a carrier wave received from a network such as the Internet, or other forms of ROM or RAM either currently known or later developed. Further, although specific components of the system have been described, one skilled in the art will appreciate that the system suitable for use with the methods and systems of the present invention may contain additional or different components.

The present invention relates to a method and an apparatus for the creation of a Radiation Dose/Quality Index (RDQI), which creates an objective and quantifiable metric for correlating the variables of radiation dose and image quality. The derived index provides for an objective measure of simultaneously quantifying radiation safety and image quality, while taking into account a myriad of contributing variables. These data can in turn be recorded in multi-institutional RDQI databases, which provide a mechanism for patient and practitioner education and training, automated decision support, establishment of best clinical practice guidelines, and methodology for comparative assessment of technologies.

The objective methodology for measuring, reporting, and analyzing radiation dose and quality have been described in U.S. patent application Ser. No. 11/976,518, filed Oct. 25, 2007, from which the present application claims priority, and in U.S. patent application Ser. No. 11/412,884, filed Apr. 28, 2006, U.S. patent application Ser. No. 12/453,268, filed May 5, 2009, U.S. Pat. No. 7,532,942, issued May 12, 2009, U.S. Pat. No. 7,831,445, issued Nov. 9, 2010, U.S. Pat. No. 7,853, 476, issued Dec. 14, 2010, U.S. patent application Ser. No. 11/699,344, filed Jan. 30, 2007, and U.S. patent application Ser. No. 12/213,184, filed Jun. 16, 2008.

However, the present invention contains several different components which can be used on an individual or collective basis, such components including 1) a radiation dose calculator, 2) objective quality assessment tool, 3) an individual and collective database(s) (Radiation, Quality, Clinical), 4) decision support features, 5) supporting technologies, and 6) outcomes analysis, which provide an objective and quantifiable metric for correlating the variables of radiation dose and image quality.

Radiation Dose Calculator

The first component, the Radiation Dose Calculator (see co-pending U.S. patent application Ser. No. 11/976,518), functions to calculate the radiation dose exposures associated with an imaging examination. This calculation can be performed following completion of the examination or prior to examination performance, based upon the various data inputs provided. An alternative to the calculated radiation dose estimate is the actual radiation dose measurements, which can be directly derived from the Quality Assurance Sensor (see U.S. patent application Ser. No. 12/453,268, filed May 5, 2009).

Regardless of the methodology employed (i.e., mathematical calculation or direct measurement), the resultant data is recorded into the database 109, 114 by the program 110 and readily available for retrieval and analysis. A properly credentialed end-user, who can be authenticated at the level of the modality (e.g., CT scanner 21) or information systems technology (e.g., PACS 30) using Biometrics (see U.S. Pat. No. 7,593,549, issued Sep. 22, 2009), can review this data and either individually or using the program 110, can determine the optimal examination protocol and acquisition parameters at the point of care, based upon the examination being performed, clinical indication, patient imaging and radiation history, and technology being utilized.

Quality Assessment Tool

The second component of the present invention is the Quality Assessment (QA) tool, which can also take a number of different forms. One tool used for objective assessment of image quality has been described in pending (Automated Quality Assurance) U.S. patent application Ser. No. 11/412, 884, filed Apr. 28, 2006, which entails a series of computerized algorithms used to measure multiple individual QA parameters including motion, artifacts, contrast resolution spatial resolution, exposure, and positioning. The data derived from this computerized analysis is performed at the point of image capture and provided to the acquiring technologist.

In addition, the corresponding image quality data is recorded into an image quality database 109, 114 for various analyses by the program 110 (e.g., education and training, technologist and departmental performance, establishment of best clinical practice guidelines, and decision support). Although the objective image quality is performed "after the fact", the derived data contained within the image quality database 114 can, however, be reviewed and utilized by the program 110 to determine optimal acquisition parameters in the future (i.e., for a given examination type, technology, clinical indication, and individual patient), thereby creating a prospective decision support tool.

As an example, a technologist preparing to perform a chest radiograph on a given patient, can query the image quality database 114 of that specific patient and the program 110 can identify the acquisition parameters utilized on a comparable examination with the highest recorded image quality measures for exposure. This would effectively provide an automated means to optimize current image acquisition using historical image quality data, specific to the anatomic region, modality, exam type, individual patient, and clinical indication. Since the ordering data is readily available prior to the time the current examination is actually being performed, this computerized analysis can be automatically done by the program 110 and made available to the technologist at the time of patient and examination authorization (using Biometrics). The system 100 can be programmed to integrate these optimized acquisition parameters as "defaults", so that the optimal exposure parameters are automatically presented to the technologist at the time of sign in to the computer system 100.

In addition to the Automated QA method of measuring image quality, the QA Sensor 23 provides an alternative means of objective image quality assessment. The QA Sensor 23 is a portable device which is directly applied to the patient at the time of image acquisition, and records specific QA metrics during the examination (e.g., motion, exposure, spatial and contrast resolution). Since the QA sensor 23 works in real-time and is specific to each individual patient and examination, the resultant data is customizable by the program 110 and automatically recorded by the program 110 in an image quality database 114 for analysis (which would be similar in functionality to the analysis described using the Automated QA method). One of the important benefits of both methods (Automated QA and QA Sensor) is that imaging examinations with multiple images or anatomic regions can be individually evaluated and have acquisition parameters customized to each individual portion of the examination.

An example would be a four view, lumbar spine radiograph which contains frontal, lateral, and oblique views. The optimal exposure parameters for the frontal and lateral views would be different from one another due to differences in soft tissue thickness, which would be exacerbated in large/obese patients.

Another example of this customization feature for optimizing image quality and acquisition parameters would be a CT examination of the chest, abdomen, and pelvis. Each individual anatomic region (containing different organ systems) can be selectively optimized by the program 110 based upon the data recorded from prior studies, in a context and patient-specific fashion. Since the context for examination performance (e.g., clinical indication) can be different from one anatomic region to another, it is important to factor this contextual data into the analysis, in order for the program 110 to optimize acquisition parameters for each individual region. In the example of the chest, abdomen, and pelvis CT, the chest CT was being performed to evaluate a chronic cough, while the abdomen/pelvis CT was performed to evaluate unexplained weight loss and diarrhea. Based upon the differences in clinical context for each anatomic region, optimal exposure parameters and image processing would vary.

An alternative method of measuring image quality using the QA Sensor 23 would be performing a test exposure. This test exposure would be performed using the radiographic apparatus 21 and an image would be obtained using a relatively small fraction of the conventional dose for the study (e.g., 5%). This initial test image could be evaluated in an automated fashion by the program 110, semi-automated or manual fashion. Evaluation would be made of, for example, peak signal to noise ratio (PSNR), patient positioning, motion, contrast and artifacts, etc. The exposure parameters would then be adjusted by the program 110 after the optimum settings were determined by the program 110 from the test image. Specifically, the detector 23 or acquisition device 21, or patient, would be repositioned if the patient positioning were determined to be incorrect. The patient could be instructed to better hold his/her breath or suspend motion. The exposure milli-Amperes (mAs) could be adjusted by the program 110 or manually, to produce a given level of predicted signal-to-noise based on the test image and contact could be optimized by adjusting the kVp settings as well, after determination of the image contrast was performed. These analyses could be performed by the program 110 using an automated image analysis tool or in a semi-automated fashion with input from the technologist. This could be done for either conventional radiography or for CT studies. This would be performed in patients that had not had a prior similar study or in patients where there had been a significant change in patient body habitus.

In another embodiment, the additional use of the QA Sensor 23 which could determine the actual radiation exposure to the patient during the test image to supplement the amount of noise measured in the test image by the program 110, in addition to the other parameters. This actual exposure value could then be utilized by the program 110 to refine the estimate of the optimal exposure and energy settings utilizing a formula which would adjust those settings for the actual, rather than the estimated or intended dose, from the imaging device 21.

For both of the above methods, determination of "acceptable" noise levels would not be a one size fits all approach, but would require consideration of multiple factors including (but not limited to) examination type, patient profile, clinical indication, technology utilized, and historical imaging studies, when available. A mathematical model could be created by the program 110 which takes these factors into consideration and continuously updates what is deemed "acceptable" in accordance with clinical review and feedback by the clinical end-users (e.g. radiologist, clinician).

In the present invention, defining quality requirements for a given patient, examination, technology, and clinical indication, is a dynamic process. In current practice, a pre-defined quality threshold is defined and the goal is to create imaging data which fulfills or exceeds this quality threshold. With the present invention, the defined quality threshold is dynamic and becomes customized in accordance with specific examination, patient, end-user and technology attributes.

As an example, a patient who is undergoing a first time chest CT exam for new onset of cough would require a diagnostic imaging dataset of high quality (e.g., 1 JND), in order to ensure that all pathology in the lungs, soft tissues, vascular structures and bones are adequately visualized. If, on the other hand, the same patient is undergoing a 3-month follow-up chest CT for a known lung cancer undergoing chemotherapy, the quality threshold would be lowered by the program 110, due to the fact that the entire thorax had undergone recent diagnostic evaluation. Since the current examination is targeting known pathology (e.g., lung mass), it does not require the same spatial and contrast resolution as in the previous study. As a result, the quality threshold for the current study is adjusted downwards by the program 110 (i.e., less rigorous quality requirements), thereby allowing for acquisition parameters to be used which could result in less radiation dose. The determination of what degree the quality threshold could be adjusted by the program 110, would be dependent upon a number of factors including (but not limited to) the type of technology being used (e.g., CT scanner), the time interval between current and prior imaging studies, patient attributes (e.g., body habitus, compliance), the context of the exam (e.g., clinical indication, prior imaging report findings, documented diseases), and attributes of the interpreting radiologist (e.g., education and training, clinical experience, pre-defined quality requirements, historical diagnostic accuracy). The ability to dynamically adjust imaging quality requirements in accordance with these multiple variables is an important part of the program 110 of the present invention, which ultimately provides an objective comparative measure for imaging consumers (i.e., patients, payers, referring clinicians), to determine the safety and quality deliverables of individual imaging providers relative to their peers.

In another embodiment, which is directed to objectively determining image quality, the present invention takes advantage of the fact that most patients have multiple historical images within their medical imaging folders. These historical images would have been performed using conventional acquisition parameters and consequently a test image would not need to be obtained in these patients. A similar calculation would be performed by the program 110 to determine optimized imaging parameters based on the prior examination. A test image could still be obtained, if desired, by the program 110, to determine whether patient positioning is satisfactory. Sample images from this "prior" imaging examination can be used by the program 110 for prospective determination of optimal acquisition parameters, based upon each individual patient, clinical indication, and examination type.

In another embodiment of the use of a test image or previous study, by the program 110, to determine optimal peak signal-to-noise ratio and radiation dose, as well as kilovoltage (kVp), would be to utilize a perceptual model to estimate the ability of an observer to perceive the impact on image quality with reduced doses. This would consequently not depend on signal to noise (PSNR) but the program 110 would instead employ a perceptual model that would rely on a visual discrimination model.

Using this approach, the test image or the previously obtained image would be utilized by the program 110 as a best standard, and progressively higher noise images would be generated by the program 110 introducing noise into the image to simulate lower exposure studies. These images would then be evaluated by the program 110 for perceived differences from the original image, and an image would be selected by the program 110 that was within a prescribed range of just noticeable difference (JND). This could be performed more quickly if an interpolation estimate was made by the program 110 with a limited number of synthesized low dose images to attempt to approximate a given JND.

For example, using a "standard" mammogram image (which are routinely acquired on patients within a certain age group an annual basis), incremental noise levels can be introduced by the program 110 into a prior mammography image at pre-defined increments relative to the calculated noise level of the "standard" image. If the calculated noise level of the "standard" image is defined as x, sequential noise levels can be created representing 75% x, 50% x, 25% X, 12.5% x, etc. The JND metric would then be applied by the program 110 to compare the original image obtained at dose x to synthesized images that with the introduction of noise by the program 110, simulated the appearance of the same mammogram obtained at various lower doses. Then, an optimal dose could be selected by the program 110 that did not differ from the original by a perceptible amount greater than, for example, 1.5 JND. This would have the effect of allowing a dose reduction with an acceptable, but minimal level of loss of perceptible image fidelity.

In general, the determination of these optimized acquisition parameters by the program 110 would be specific to each individual patient, the anatomic region of interest, and the modality being performed. In addition, the program 110 could introduce an additional level of quantification into the analysis which takes into account the clinical context of the examination being performed.

An illustrative example includes a chest radiograph (CXR) performed on the same patient but under three different clinical circumstances, as follows:

1) CXR for determination of feeding tube position;
2) CXR performed for routine screening (e.g., yearly physical exam); and
3) CXR performed for weight loss and cough (e.g., suspicious for occult cancer).

This examination would include the same patient, exam type, and anatomic region. On the surface one would therefore, assume that the optimal exposure parameters using the JND metric (or PSNR) would be identical. The variable not considered, however, is an important distinction between these three different exams, i.e., the clinical context.

In the first case (feeding tube placement), the purpose of the study is to locate a newly positioned feeding tube. This task can be reliably performed in the presence of significant noise and as a result, can utilize a lower radiation dose and still fulfill the desired clinical indication. At the same time, this patient probably had a recent CXR within the past 48 hours (since most patients with line placements undergo serial radiographs). As a result of the clinical indication and recent comparison study, the program determines that the "acceptable" levels of noise could be fairly high (e.g., 2 JND). The clinical determination of "acceptable noise", which would translate into the defined quality threshold and number of acceptable JNDs, can be derived mathematically by the program 110 from multiple variables including the technology being utilized, the patient profile, clinical indication, anatomic region, exam type, and timing of comparable imaging studies. This would allow a dose reduction by the program 110, tailored to a perceptual model as well as a clinical model, where the program 110 would allow greater levels of perceived loss of image quality when this was deemed acceptable, depending on the indication for the examination and type of study being performed.

For the second and third examples (e.g., routine screening and occult cancer), one can see that these would also represent differences in a clinical context. The screening exam would be "low probability" for underlying pathology, especially if the patient's past medical history was unremarkable. The diagnostic exam for occult cancer, on the other hand, would be deemed "high probability", based upon the reported symptoms and concern for cancer, which would require higher levels of image quality. One can understand that the clinical context for the exam is an important determinant in defining "acceptable" noise and image quality requirements. The goal is to optimize radiation safety (i.e., dose reduction), while maintaining acceptable levels of image quality.

Databases

Once the radiation dose and quality metrics have been determined, the next components are the various databases 114; which track radiation, quality, and clinical data. The various data recorded in the radiation portion of the database 114 include: 1) exposure parameters utilized for acquisition (kilovoltage (kv) and mA); 2) dose optimization techniques employed (e.g., real-time dose modulation); 3) exposure time; 4) acquisition speed; 5) radiation exposure index value; 6) subject to image distance (SID); 7) subject to object distance (SOD); 8) number of images acquired; 9) image object descriptor (IOD); 10) exam type (imaging modality specifications); 11) anatomic region; 12) patient body habitus (height, weight, thickness); 13) entrance surface dose (a derived calculation); 14) dose area product (a derived calculation); 15) critical organ dose (a derived calculation); and 16) type and quantity of pharmaceuticals administered (nuclear medicine).

These data provide the necessary requisites for determining radiation dose exposure for the specific examination performed; taking into account the specific technology being utilized, unique characteristics of the individual patient, and anatomy being imaged. From this data, a number of data-derived analytics from the radiation technical data can be created by the program 110, including: 1) current exam type and dose calculation; 2) specialized dose reduction techniques employed; 3) radiation dose "savings" (comparison of current dose with reference dose); 4a) mean dose for conventional/standard technique (same examination type); 4b) mean dose for alternative imaging exam (based on clinical indication); 4c) mean dose of alternative technology for same exam type (e.g., film/screen mammography); 4d) mean dose of local, regional, and national reference standards; 5) itemized medical imaging and radiation dose history; 6) cumulative lifetime radiation dose calculation; and 7) calculation of lifetime carcinogenesis risk.

In addition to the exam-specific radiation dose, a number of comparative analytics can be recorded by the program 110, which serve as important barometers of dose reduction including (but not limited to) supporting technologies used to facilitate maximal dose reduction (e.g., noise reduction filters), calculation of relative radiation dose savings (e.g., comparing technical data of the current examination with those of comparable reference default standards), and cumulative patient-specific radiation dose measurements and carcinogenesis risk. These latter values provide an important reference in determining the criticality of radiation dose reduction for each given patient.

As an example, an oncology patient who has undergone repetitive CT examinations over the course of their diagnosis, treatment, and follow-up surveillance may have over time accumulated an exceedingly large cumulative radiation dose, placing them at heightened risk for radiation-induced carcinogenesis. The program 110 would present this data to both the imaging provider (e.g., radiologist) and referring physician at the time of order entry and exam protocol. This enables all responsible parties to be aware of the specific patient's radiation history, relative risks, and available options for intervention. If, for example, the clinician was to be presented with this data by the program 110 at the time of order entry, he/she may elect to evaluate alternative imaging tests which could avoid or reduce radiation exposure. In the case of an oncology patient who is being routinely evaluated for disease recurrence in the setting of treated liver metastasis (from colon carcinoma), the program 110 may present the clinician with the following imaging alternative imaging options:

1) Ultrasound
   a) Advantages: No ionizing radiation.
   b) Disadvantages: Limited in assessment of bowel and lymph nodes. Can be limited by patient body habitus and operator dependent.
2) MRI
   a) Advantages: No ionizing radiation.
   b) Disadvantages: Expensive (2-3× cost of CT). Can be limited by motion.
   c) Contraindications include pacemaker (which this particular patient has).
3) Ultra-Low Dose CT
   a) Advantages: Can reduce radiation dose by 10× that of conventional CT.
   b) Disadvantages: Can adversely affect quality due to excessive noise.

After being presented with this radiation data by the program 110, the referring clinician and/or radiologist may elect to opt for one of the presented options, taking into account the specific patient profile, imaging history, clinical indication, and available technology. In reviewing the past imaging database 114, the two most recently performed CT reports have shown the patient to be free of disease, which places the patient at a relatively low risk of tumor recurrence. As a result, the referring clinician elects to change the order to ultrasound, in order to concentrate imaging on the primary organ of choice—the liver.

Alternatively, if the clinician was to order CT but place a request for maximal radiation dose reduction, the radiologist may elect to perform a targeted examination of the upper abdomen only, select a protocol using maximal dose reduction, and employ a program 110 with specialized image processing and filters for noise reduction. This illustrates that the program 110 has multi-functionality, to record data relative to each imaging examination and individual patient, provide analytics for informed decision making, and provide computerized decision support to enhance outcomes.

The database components specific to image quality would be variable and dependent upon the specific technology utilized for quality assessment. In the examples of the QA Sensor and Automated QA tools, the specific data recorded in the (quality) database 114 by the program 110, include: 1) anatomic coverage; 2) positioning; 3) collimation; 4) contrast resolution; 5) spatial resolution; 6) density and measurement calibration; 7) noise (image uniformity); 8) image processing (and reconstruction); 9) artifacts; 10) registration of disparate datasets; 11) motion; 12) contrast enhancement; and 13) comprehensive quality score (a derived calculation).

These data would in effect create a computer program-derived list of quality-centric metrics which can be acquired through direct measurement (e.g., microprocessors) or analysis (e.g., computer algorithms). These individual quality data can be pooled by the program 110 to provide a comprehensive quality score, which can be validated through clinical feedback provided by clinical providers (e.g., technologist, radiologist, and clinician). The individual and collective data measures recorded in the database 114 by the program 110 would create an iterative model where objective and subjective quality scores could be collectively analyzed by the program 110 to refine the methodology in which image quality is graded. As the database 114 becomes populated with increasing data, the scoring of collective quality by the program 110 becomes constantly refined, with subjective correlation of image quality provided by multiple end-users, institutions, and technology providers.

If an alternative method of measuring image quality is selected (e.g., JND metric), direct quality measures would not be created by the program 110. The analysis by the program 110 would instead center on determination of the lowest radiation dose which satisfies the defined quality threshold. Determination of the "minimum quality threshold" is largely the result of clinical data analysis by the program 110. In this analysis, the program 110 attempts to define the lowest quality which can satisfactorily answer the clinical question prompting examination performance, without sacrificing clinical outcomes. A number of variables contribute to the determination of this "minimum quality threshold" (MQT) and the data recorded by the program 110 in the clinical database 114 includes: 1) clinical indication; 2) past medical/surgical history; 3) current medical problems; 4) ongoing treatment (including medications); 5) historical imaging studies; 6) patient profile; 7) imaging exam type and positioning; 8) anatomic region; 9) radiologist/clinician profile; and 10) supporting technologies.

In order to illustrate how this clinical database 114 would be used to determine the MQT, two examples are discussed. These examples will include 1) an intensive care unit (ICU) chest radiograph for line placement, and 2) a chest CT for lung cancer.

In the first example, the portable ICU chest radiograph is being performed on a critically ill patient, with the clinical requirement of evaluating placement of a support line. The ability to visualize line placement is dependent upon the imaging modality (chest radiograph), examination positioning (supine portable), patient body habitus (large, edematous) specific type of line (central venous catheter), and anatomy (chest) being analyzed. Additional factors which come are relevant include the individual patient's medical/surgical history, underlying illnesses, treatment, and historical imaging examinations.

For example, this same patient has had three recent chest radiographs performed over the past 24 hours. Barring a dramatic change in the patient's clinical condition, one would deduce that all relevant imaging data has been recently assessed and the current study only requires visualization of the newly positioned line. Any potential pathology in the lung fields, soft tissues, or bony skeleton would have been previously recorded by the program 110 in the database 114. As a result, the MQT is lower (in the presence of recent correlating imaging studies), than would be the case in a patient without a baseline imaging exam.

At the same time, if the line placed is radio-opaque, then visualization should be relatively straightforward, and the requisite MQT would be correspondingly low. If the program 110 was to supplement line detection with computer-aided detection (CAD) software which localizes the line termination, then further reduction in the MQT could be tolerated, and still accomplish the stated clinical goal. As each piece of supporting data is factored into the analysis by the program 110 (which can be driven through artificial intelligence techniques, such as neural networks), a more exact MQT can be determined by the program 110.

To supplement the computer-derived MQT, end-user input can be utilized by the program 110 to create a computer program/human-derived MQT, which is specific to the medical imaging examination, individual patient, and clinical context. Human input can take place both at the "front" and "back" ends of MQT determination. In the "front end" analysis by the program 110, the radiologist provides his/her MQT score based upon the presenting clinical data, while "back end" analysis by the program 110 provides end-user input following completion of the imaging examination.

If, for example, the radiologist interpreting the CXR, ascertains that the image presented for review is of insufficient quality, he/she can provide input into the clinical database 114, which is then factored by the program 110 into future MQT analyses. One method of end-user input would consist of a pop-up menu by the program 110, which asks the clinician or radiologist to rate whether sufficient image quality was present to support clinical management and interpretation. The available options for such a pop-up menu of end-user input options for "back end" MQT program analysis, include: 1) sufficient quality; 2) insufficient quality—a) minimal quality insufficiency (i.e., clinical analysis is minimally compromised due to quality limitations); b) moderate quality insufficiency (i.e., clinical analysis is moderately compromised due to quality limitations); and c) maximal quality insufficiency (cannot perform requisite clinical analysis, repeat exam required).

Based upon this specific end-user quality feedback, two subsequent actions are taken with respect to MQT analysis by the program 110. Firstly, future imaging exams (specific to the modality, anatomic region, clinical indication, and patient) will be adjusted by the program 110 to take into account the end-user input. Secondly, an end-user profile will be created by the program 110 for the specific radiologist/clinician providing input.

If, for example, one radiologist deems an imaging study's quality to be sufficient, while another radiologist deems the same study's quality to be moderately insufficient, then their respective profiles will be recorded in the MQT database 114 by the program 110. In the future, as new imaging examinations are being performed by the program 110 (and MQT scores derived), the profile of the respective radiologist or clinician responsible for image interpretation or clinical management can be factored into the MQT analysis by the program 110. This provides important information within the RDQI database 114 by the program 110 for patients or clinicians who are using the data for the selection of imaging providers. A patient who is highly concerned about radiation exposure may search for an imaging provider (at a departmental of individual radiologist level) who has the most efficient RDQI scores. Another patient may be less concerned with maximizing radiation dose reduction, but instead focuses almost exclusively on quality scores independent of radiation dose. Both data analyses can be derived form the comprehensive RDQI database 114 by the program 110, and assist in education, training, and service selection.

In the second example (chest CT for lung cancer screening), a different patient profile and clinical indication exist. Since lung cancer detection can be highly sensitive to variation in image quality, and misdiagnosis has a significant impact on clinical outcome (i.e., morbidity and mortality), higher quality requirements would be required for this examination by the program 110. Other factors which would influence the MQT would include patient body habitus (which affects noise), historical imaging studies (which improve early detection by offering temporal comparison), and supporting technologies (e.g., CAD to assist in nodule detection).

Decision Support

The decision support features of the program 110 operates by providing statistical data to the end-user to improve decision-making at the point of care. Suppose for example, a CT technologist is trying to identify the optimal exposure parameters for a given anatomic region (e.g., pelvis) and clinical indication (e.g., trauma). The program 110 can review prior CT exams performed on that same patient, along with comparable exams on other patients within the multi-institutional database 114. Based upon the clinical indication and organ system of interest, the computer program 110 ascertains that optimizing exposure parameters and determination of the MQT is largely due to a single clinical factor—bone mineral density. The decision support feature of the program 110 can automatically activate a query of the specific patient's electronic medical record (EMR) to determine if a bone mineral density (BMD) measurement is available for correlation. If this measurement is readily available, it is automatically recorded by the program 110 into the database 114 and correlated with CT acquisition data from patients with similar BMD measures. Based upon this multi-institutional analysis, optimal exposure parameters are presented by the program 110 to the technologist based upon the given BMD, anatomic region of interest, clinical indication, CT technology being utilized, and radiologist profile.

If the patient in this example does not have a documented BMD measurement in his/her EMR, one option is for the program 110 to query that particular patient's historical imaging folder to identify recently performed imaging studies, which may be relevant. In this particular case, the patient had recent radiographic studies of the lumbar spine (performed 6 months earlier), chest (performed 12 months earlier), and ankle (performed 24 months earlier). The program 110 provides these options to the technologist, who in turn selects the imaging study of greatest relevance (lumbar spine radiographs). Once selected, the images from this lumbar spine exam are automatically retrieved from the database 114 by the program 110 (along with the corresponding report). The CT technologist is now presented by the program 110 with correlating image data from the patient's historical imaging folder to assist in the determination of optimal exposure parameters. The technologist is presented with two options from the program 110:

1) input a subjective measure of BMD into the database 114, based upon the historical images;
2) allow the computer program 110 to derive a BMD estimate from the historical images, and to save same in the database 114.

With the assistance of the radiologist, the technologist provides a subjective measure of BMD (severe osteopenia), which in turn in used by the program 110 to derive optimal exposure parameters. This illustrates how the program 110 facilitates data-driven decision making, by utilizing data contained within the database 114, data within the patient EMR database 10, and multi-institutional RDQI data.

Supporting Technologies

Supporting technologies are an integral part of the program 110. These can take a number of different forms and can include technologies aimed at improving image quality at reduced radiation dose exposures (e.g., noise reduction filters), technologies that manipulate or accentuate the medical imaging data for enhanced detection (e.g., specialized image processing), or technologies which improve interpretation accuracy of imaging datasets in the setting of radiation dose reduction (e.g., low dose computer-aided detection (CAD) software). The common denominator of these supporting technologies is improved RDQI efficiency, namely where the program 110 provides higher image quality at lower radiation dose.

The program 110 also serves an objective means of testing and validating new technologies and quantitatively analyzing their impact on radiation dose reduction and quality. Essentially all technologies in the imaging chain can be objectively analyzed by the program 110 to determine their respective contribution on the overall RDQI. As an example, a new digital radiography detector 21 (used for image acquisition) can be tested by the program 110 to see whether it provides enhanced image quality at lower radiation doses than competing detectors 21. At the same time, a new CAD program (used for image interpretation) can be tested to correlate its diagnostic accuracy performance at different levels of radiation dose.

Outcomes Analysis

The program 110 can also use the data contained within the databases 114 to play a fundamental role in defining data-driven best clinical practice guidelines, which is the cornerstone of evidence based medicine (EBM). If one was to track radiation and quality with clinical outcomes using the program 110, a reliable mechanism would be available to create medical standards for optimal medical practice. In the example previously cited of the chest CT for lung cancer detection, one may find that certain patient profile characteristics (e.g., smoking history or genetic markers) may be associated with lung cancers which are only detectable at certain MQT scores. As a result, patients who exhibit these specific profile characteristics would have a predefined MQT score which must be maintained, regardless of the technology employed, radiologist/clinician preferences, or presence of comparison imaging studies.

Alternatively, data from the RDQI database 114 may show that certain types of technology (e.g., CT scanner 21) are associated with earlier lung cancer detection at slightly higher MQT scores than those of competing technologies. In this scenario, the data would dictate that imaging providers using that specific technology (e.g., CT scanner of vendor A) for that particular clinical indication (e.g., suspected lung cancer) maintain a pre-defined MQT score which is slightly higher than another imaging provider using a competitor's CT scanner for the same clinical indication. In the end, the purpose of the data analyses by the program 110 is to improve clinical outcomes by creating data-driven standards identifying best practice guidelines. In turn, these same databases 114 can be used by the program 110 to facilitate the creation and refinement of technologies which further improve technical and clinical performance.

An integral end-product of the data collection and analysis would be the creation of standardized data by the program 110, related to radiation exposure and quantified image quality. The recording of this data in the database 114 by the program 110 would be independent of individual vendors' technologies; including acquisition devices (e.g., CT scanner), image processing software; and information systems (e.g., PACS, EMR). The derived dose/quality measurements could be comparatively analyzed by the program 110 in several different ways. One way would be for the program 110 to create a mathematical ratio of quality divided by radiation exposure, so that the higher the value, the greater the efficiency of radiation dose and image quality.

An alternative method of expressing this concept would be for the program 110 to create a standard metric referred to as the "quality per unit dose", where the program 110 takes a quantitative measure of image quality and divides by the radiation dose exposure.

Regardless of the method employed, the ultimate goal is to create a standard and objective methodology for correlating radiation dose and image quality; in order to quantify the often competing demands of optimizing patient safety (radiation exposure) and medical image quality simultaneously.

While the primary goal of the program 110 is to record, track, and analyze quality and radiation data specific to individual imaging exams and patients; a number of analytics can be derived which can be used to assess the performance of various stakeholders. On an individual healthcare provider basis; medical physicists, technologists, QA specialists, radiologists, and clinicians all play important roles in determining medical imaging quality and safety, as it relates to the various steps of ordering, exam selection, protocol optimization, acquisition, image processing, quality assurance, equipment quality control, and diagnostic interpretation.

Another individual who plays an important role in determining quality and safety is the patient, who is important in providing pertinent clinical and historical data, and whose compliance is an important determinant in quality and safety. As an example, a patient who does not follow instructions during the course of CT acquisition, may produce motion artifact, which adversely impacts image quality, may result in repeat acquisition (with greater radiation dose), and detracts from diagnostic accuracy.

The technology being used is an important factor determining quality and safety, and includes not only the medical acquisition devices 21 (e.g., CT scanner, mammography unit), but also information system technology for data analyses (e.g., PACS 30, RIS 20, EMR 10) and imaging processing software (e.g., low dose filters, smoothing algorithms).

On a larger level, institutional providers of imaging services can be analyzed by the program 110 to determine their collective performance relating to medical imaging quality and safety. This institutional analysis can be correlated by the program 110 with reference peer groups (e.g., academic tertiary care hospital providers, small rural community hospital providers, suburban outpatient imaging center providers) to provide consumers with objective data, which can be categorized in accordance with specific medical imaging exams (e.g., mammography, CT angiography), diseases (e.g., breast cancer, coronary artery disease), or patient profiles (e.g., emaciated, morbid obesity). This same type of collective analysis can also be applied by the program 110 to third party payers (e.g., private insurance companies), where prospective or existing customers can review objective quality/safety data to determine how individual payers' performance relates to that of competitors.

The resulting medical imaging quality and safety data can be used by the program 110 for education/training, creation of best practice guidelines, testing and validation of technology, and informed decision making.

Example

In one representative example, a patient presents for the first time to a new primary care physician with the complaint of chronic cough. The various stakeholders included in the analysis will include the patient, primary care physician (i.e., clinician), technologists, radiologist, hospital administrator, radiation oncologist, and technology provider (i.e., vendor).

At the time of clinical presentation, the patient (Mrs. Jones) reports a chronic, unrelenting cough for the past 3 months, along with an unexplained 10 pound weight loss. In taking the history, the clinician (Dr. Smith) identifies several additional variables which may be of clinical significance, including a 50 pack/year smoking history, prior diagnosis of COPD, surgical history of partial lung resection (for a benign neoplasm), and discontinuation of COPD and heart medications due to financial reasons. One of those medications Mrs. Jones has been taking for several years is used for the treatment of cardiac arrhythmia and has potential pulmonary complications. On physician examination, the clinician detects wheezing from both lungs consistent with COPD, along with pallor (suggesting underlying anemia) and a generalized diminution in strength.

In addition to the ordering of basic blood work and prescription refills for treatment of COPD, the clinician signs in to the computer system using Biometrics.

Figure 2A:
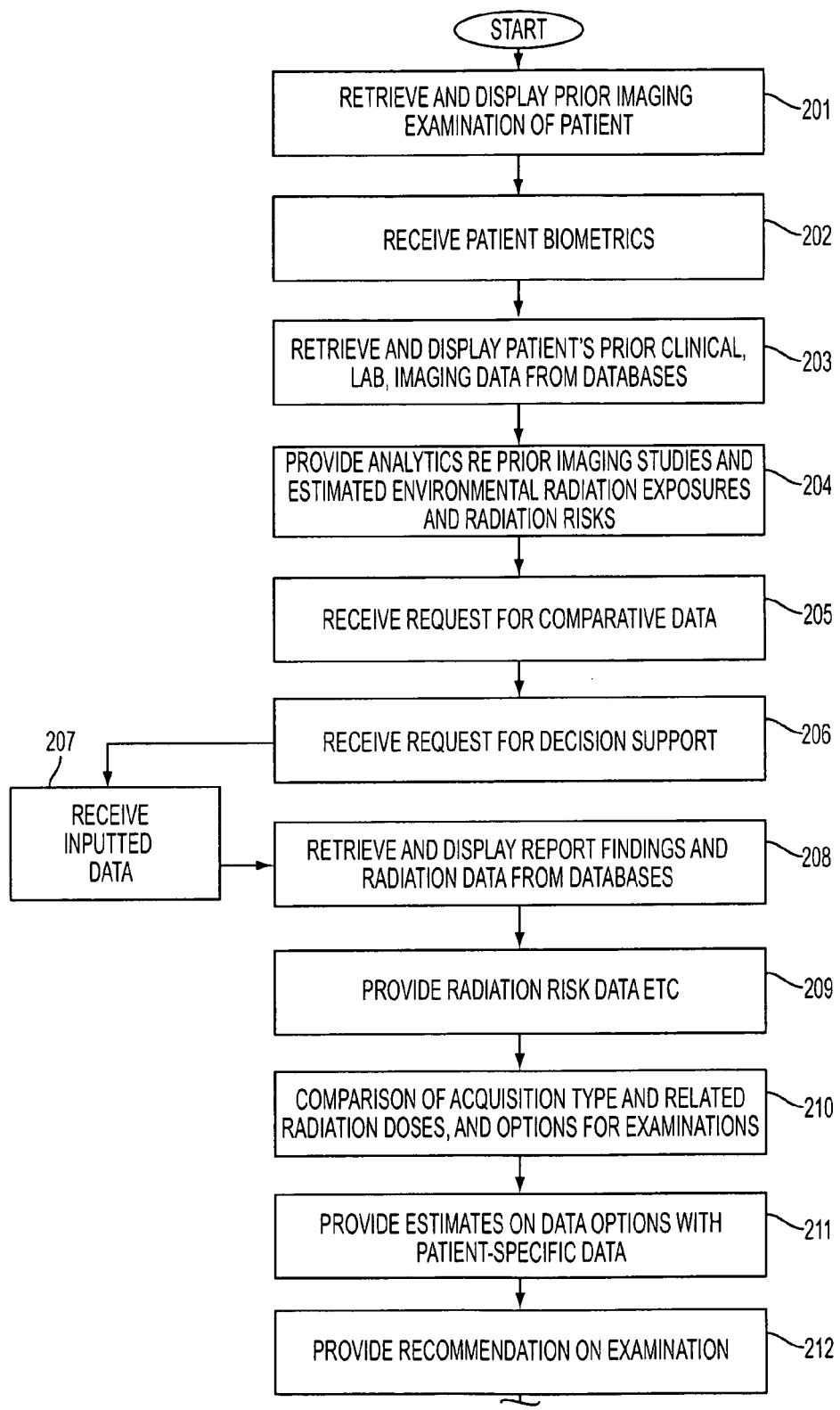
FIGS. 2A and 2B are a flowchart of a method for determining acquisition parameters in a medical imaging examination, according to one embodiment consistent with the present invention.
Figure 2B:
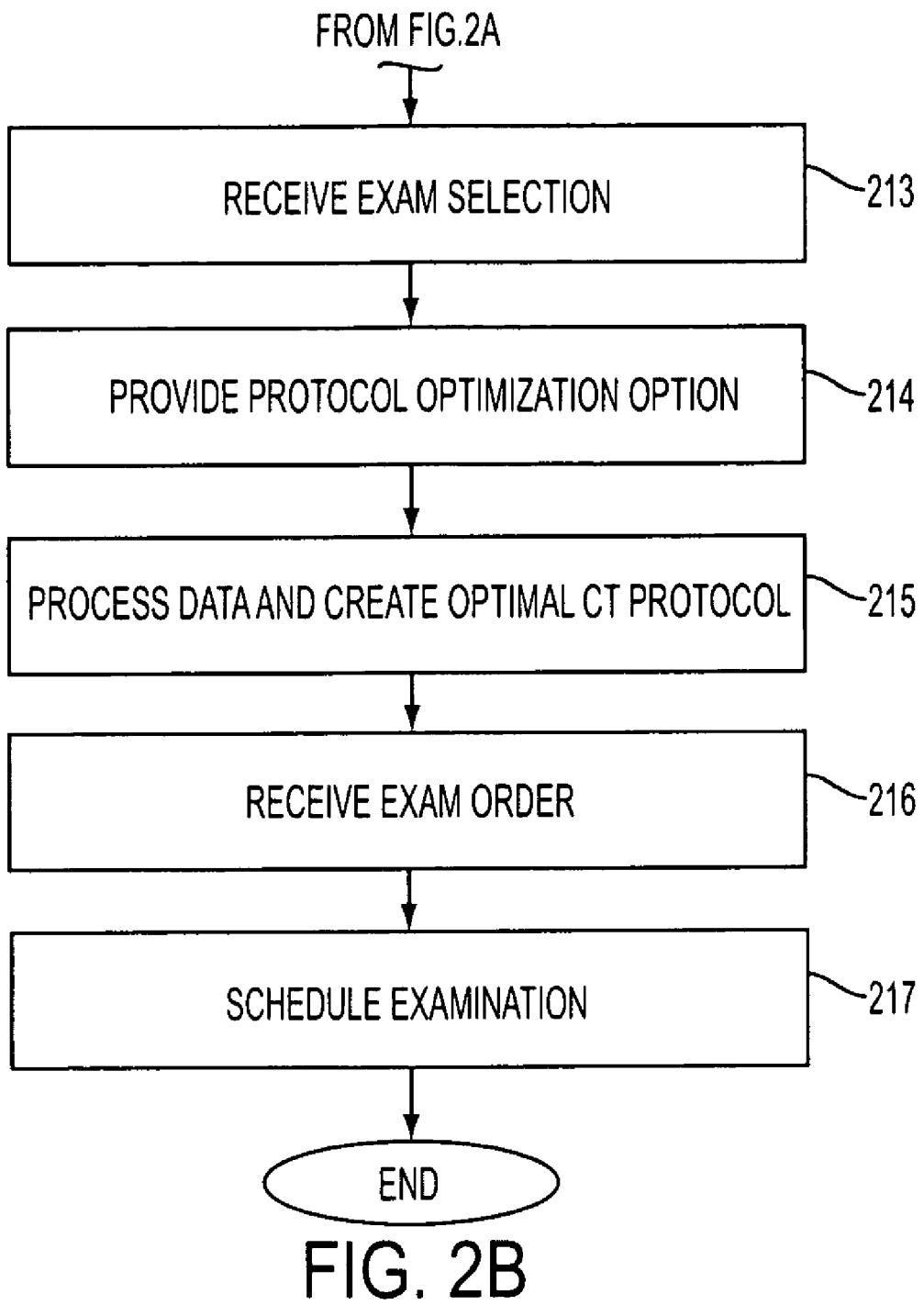

In step 201 (see FIG. 2A), the clinician orders, and the program 110 retrieves and displays, the prior imaging examination folder of the patient from the database 114. However, in this case, since the patient has never been seen before by this particular physician, their prior imaging exam folder is not immediately accessible.

Upon further questioning of Mrs. Jones, the clinician learns that Mrs. Jones has had numerous chest radiographs and CT exams over the past 10 years related to COPD, intermittent infections, and the surgically resected benign pulmonary neoplasm.

In step 202, the patient's Biometrics are inputted into the computer system 100, and in step 203, the program 110 retrieves and displays the patient's prior clinical, laboratory, and imaging data from the Biometrics EMR 10, PACS 30 and RIS 20 databases. The prior chest imaging studies, corresponding reports, and technical data are available to Dr. Smith for review, and included in the imaging data are a series of examination and patient-specific data related to individual exam radiation dose, cumulative radiation dose, and radiation iatrogenic risk.

Because Mrs. Jones has a longstanding history of COPD and a prior partial lung resection, her pulmonary status has been significantly compromised. When Dr. Smith opens up the radiation iatrogenic risk application, he is presented in step 204, with several analytics by the program 110, including the carcinogenesis risk associated with prior imaging studies, along with estimated environmental radiation exposures. Other iatrogenic risks of radiation (distinct from carcinogenesis) compiled by the program 110, include the risk of further deterioration in pulmonary status from radiation, along with concomitant pulmonary fibrosis related to the medication's therapy.

Before ordering a chest imaging study for the current complaints, Dr. Smith notes that Mrs. Jones has had a recent chest radiograph 6 months earlier, along with a chest CT 18 months earlier. While the chest radiograph report described "no interval change in COPD", the chest CT report described a "non-specific 6 mm lung nodule, with recommendation for CT follow-up in 3-4 months", which was not performed.

Upon recognizing this fact, Dr. Smith thinks it may be more prudent to order a chest CT, rather than a chest radiograph. At the same time, Dr. Smith is concerned about the extra cost and radiation exposure of the chest CT (as opposed to the chest radiograph) and queries the program in step 205, for additional comparative data, to assist him in the examination selection and ordering process.

Upon opening up the ordering decision support application in step 206, Dr. Smith is presented by the program 110 in step 207, with a number of data fields in which he is asked for a series of input data, to assist in the decision making process. The requested clinical data (and corresponding data inputs) includes the following items:
  1) Clinical Indication:
  Chronic cough and unexplained weight loss
  2) Past Medical/Surgical History:
  COPD
  surgical resection of benign lung neoplasm
  benign breast biopsy
  cardiac arrhythmia
  3) Current Medical Problems:
  COPD
  cardiac arrhythmia
  4) Ongoing Treatment (Including Medications):
  steroid inhaler
  medication
  5) Historical Imaging Studies:
  chest radiography
  chest CT
  mammography
  brain MRI
  echocardiography
  CT angiography of heart
  6) Patient Profile:
  ambulatory
  chronic smoker
  self-pay (no insurance)
  7) Imaging Exam Type and Positioning:
  request decision support
  8) Anatomic Region:
  chest
  9) Radiologist/Clinician Profile:
  clinician: family practitioner
  10) Supporting Technologies:
  unknown Based upon the above inputted data from step 207 into the database 114 provided by the clinician, the program 110, using a computerized decision support application, retrieves and displays additional information regarding the report findings and radiation data attributable to the prior imaging studies, in step 208. This data can be exported electronically from the outside institutional database (i.e., 114) to the in-house database 109, 114 by activating an electronic transfer function. Had the historical imaging data been performed at the same institution, this data transfer and analysis would have been automatically performed by the program 110, without additional actions required.

Upon receipt of the historical imaging data, the program 110 derives the following data in step 209, and provides it to the user:
  1) Individual exam radiation dose exposures.
  2) Cumulative patient radiation dose exposure.
  3) Estimated environmental radiation dose exposure.
  4) Radiation-induced carcinogenesis risk
  5) Cumulative carcinogenesis risk (taking into account all patient-specific cancer risk factors).
  6) Additional radiation risk (for non-carcinogenic disease, e.g., pulmonary fibrosis).

In the determination of the imaging examination and protocol selection, the program 110, in step 210, derives the following data (comparing chest radiography and chest CT), and also presents it to the user:
  1) Estimated radiation dose exposures.
  2) Estimated cost estimates.
  3) Comparative clinical value.
  4) Options for radiation dose reduction.
  5) Options for enhancing clinical value.
  6) Options for minimizing cost.
  7) Comprehensive cost-benefit analysis.

By activating any of the data options presented by the program 110 in step 211, Dr. Smith can get more detailed analysis by the program 110 to assist in the exam selection process. For example, if Dr. Smith was to select the "Options for radiation dose reduction" and "CT", he would have the following data presented by the program 110 in step 211:
  1) Estimated dose for conventional CT.
  2) Estimated dose for low dose.
  3) Estimated dose for ultra-low dose CT.

The estimate radiation dose is calculated using the Radiation Dose Calculator of the program 110. When incorporating the patient-specific input data into the analysis in step 211, the program-derived recommendation is for Low-dose CT, displayed in step 212, which is provided to the user with the following indicators:

1) Pre-existing history of COPD and smoking (↑ cancer risk).
2) Previously documented nonspecific lung nodule.
3) Medication therapy (frisk for pulmonary fibrosis)
4) Symptoms of chronic cough.

After selecting the option for Low-dose CT, which the program receives in step 213, Dr. Smith is presented by the program in step 214 with the decision support option of "protocol optimization".

In this option, when selected, the program, in step 215, processes the clinical, imaging, and historical data to create the optimal CT protocol to maximize radiation dose reduction, enhance image quality, and provide accurate diagnostic accuracy. The following data would be included by the program 110, in the protocol optimization schema:

1) Acquisition parameters.
2) CT kernel.
3) Collimation.
4) Image processing.
5) Noise reduction filters.

This protocol optimization schema of step 214 can be performed by the program 110 using several options. In one exemplary option, the clinician selects the option for institutional-specific protocol optimization. If Dr. Smith was to select this option for his host institution, the institutional database 114 would be searched by the program 110 and the optimal protocol designed would take into account the technologies available at the host institution, institutional-specific RDQI data, and the patient-specific clinical/imaging data.

In another exemplary option, the clinician could select the option for regional protocol optimization (and define the geographic region of interest). The computer program 110 would query the RDQI databases 114 from imaging providers within a pre-defined geographic area and identify the optimal protocol along with the location of the corresponding institution (i.e., with the available technology to perform this protocol).

In an exemplary option for all institutions protocol optimization, the computer program 110 would query the entire multi-institutional RDQI database 114 and present the optimal protocol from all participating institutions, along with all their corresponding locations.

As stated above, after selecting the option for institutional-specific protocol optimization, the host institution's RDQI database 114 is queried by the program 110, and an optimized protocol is presented on the display 102 by the program 110 in step 215, based upon the host institutions' technology, staff, and performance data.

In step 216, the examination order entry process is inputted into the computer system 100, and after completion of the order entry process, the examination is scheduled by the program in step 217, and the date and time of the CT exam is provided to the patient, along with any exam-specific instructions.

Figure 3A:
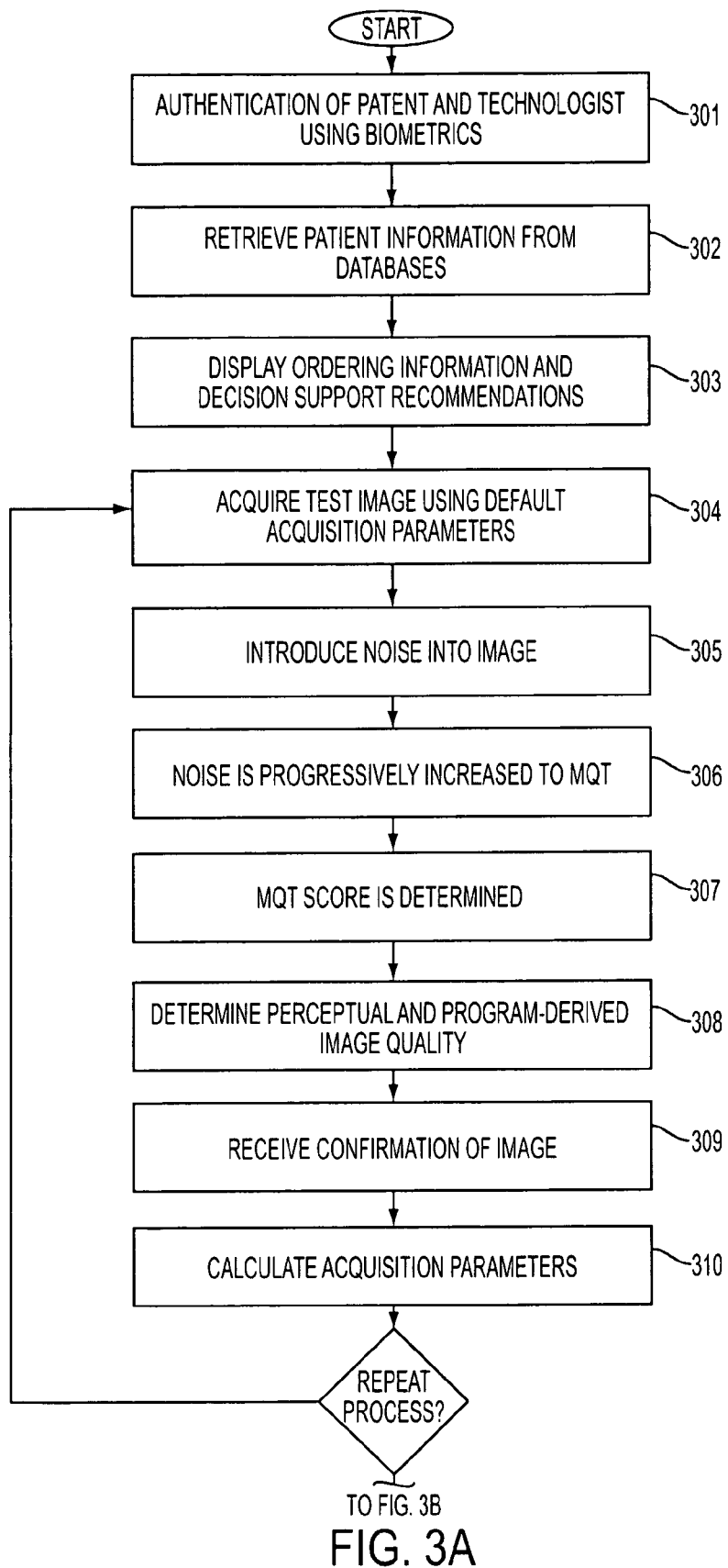
FIGS. 3A and 3B are a flowchart of a method for determining an RDQI score in quantifying radiation safety in a medical imaging examination, according to one embodiment consistent with the present invention.

The patient subsequently arrives at the imaging department of the hospital at the day and time of the scheduled CT exam. Both the patient and technologist performing the examination can undergo authentication by the program 110 of their credentials locally at the level of the CT scanner (using Biometrics), in step 301 (see FIG. 3A), and patient information is then retrieved by the program 110 in step 302 from the corresponding databases 114.

Upon retrieval of the patient information from the RDQI database 114 by the program 110, the ordering information and decision support recommendations are displayed by the program 110 in step 303, and are reviewed by the technologist. Due to the complicated clinical and imaging history, and lack of prior on-site imaging studies, the technologist requests direction from the radiologist via a communication method (i.e., email, phone, etc.). The radiologist instructs the technologist to deviate from the computer program-derived protocol recommendations and instead, determine optimal acquisition parameters using the JND metric protocol. This protocol calls for the following workflow steps by the program 110.

In step 304, the technologist acquires a sample or "test" CT image, in the region of interest (chest), using standard "default" CT acquisition parameters, determined by the quality assessment tool using the image quality databases 114. (Alternatively, the QA Sensor 23 could be used to determine the actual radiation exposure.)

In step 305, computer-derived noise is introduced by the program 110 into this test image, in order to mimic the CT appearance using low dose acquisition parameters.

In step 306, the amount of introduced noise is progressively increased by the program 110, until a pre-determined minimal quality threshold (MQT) is reached.

In step 307, the MQT score is determined by the program 110 based upon the clinical parameters, patient profile, examination being performed, technology utilized, and individual radiologist profile. In this particular example, the MQT score is determined to be the equivalent of 1 JND (just noticeable difference), by the program 110.

In step 308, the perceptual and program-derived image quality are determined by the program 110, and then the computer derived 1 JND image is reviewed by the radiologist to ensure that the perceptual and computer-derived image quality are satisfactory.

In step 309, the technologist provides confirmation of the 1 JND image, which is received by the program 110, and the computer program 110 calculates the acquisition parameters in step 310, which will produce the desired CT image quality (1 JND); and if necessary, imaging quality requirements can be dynamically adjusted by the program 110.

Figure 3B:
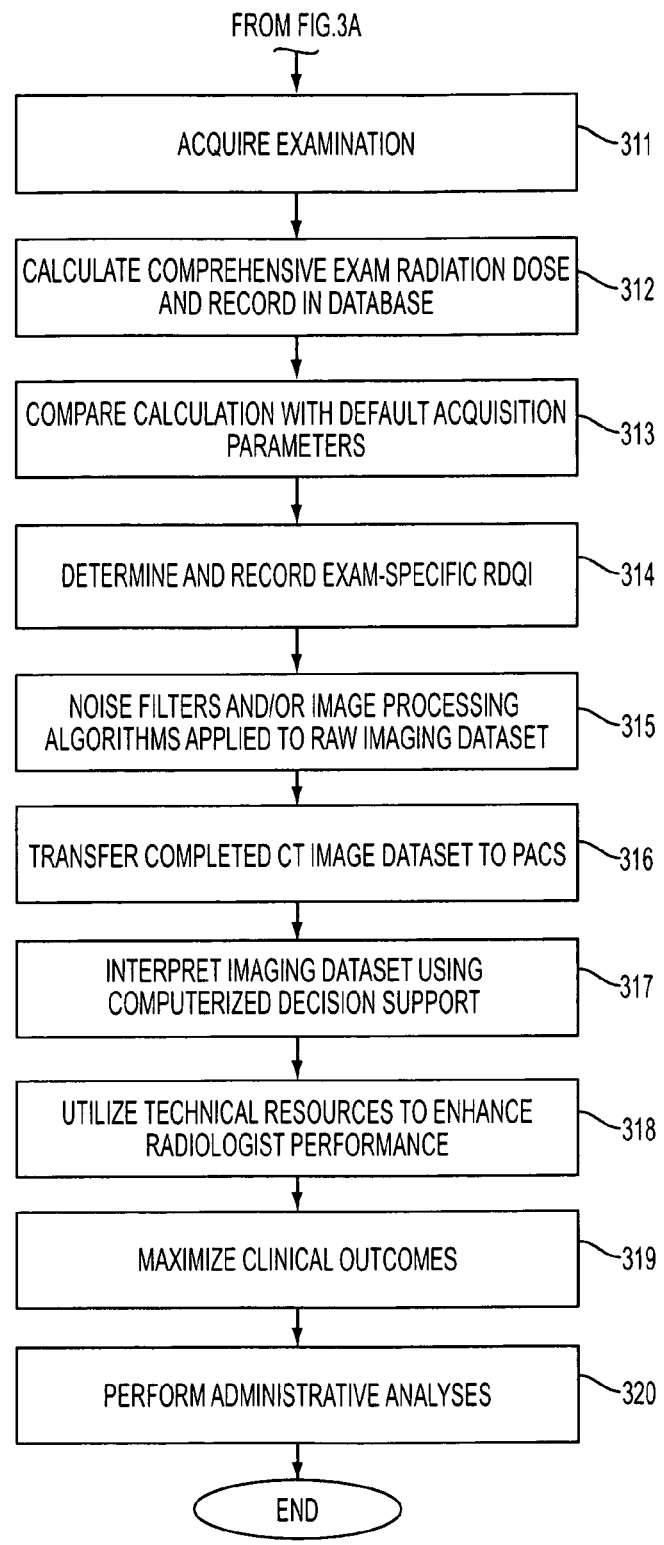

If the technologist wanted to repeat this process at multiple levels (e.g., upper lung fields, pulmonary arteries, and diaphragm) within the anatomic region of interest, he/she could do so in order to dynamically optimize acquisition parameters at multiple levels of strategic importance In step 311 (see FIG. 3B), the technologist can now acquire a full study of the patient according to the examination order.

After the acquisition step is completed, a comprehensive exam radiation dose (Radiation Scorecard) is calculated by the program in step 312, and recorded in the RDQI database 114 by the program 110.

This value can be compared by the program 110 against the computer derived "standard" radiation dose in step 313, which is calculated by the program 110 based upon standard "default" CT acquisition parameters.

An additional exam-specific radiation dose quality index (RDQI) is recorded by the program 110 in the database 114 in step 314, which reflects the total examination radiation dose and the objective measure of image quality.

In step 315, the technologist applies specialized noise reduction filters and/or image processing algorithms to the "raw" imaging dataset using the program 110, in order to decrease noise and enhance contrast resolution.

In step 316, the completed CT image dataset is then transferred by the program 110, to the PACS 30 for radiologist interpretation.

In step 317, interpretation of the imaging dataset is performed by a radiologist. Upon review of the acquired imaging dataset, the radiologist determines the optimal manner in which the imaging data is processed, reconstructed, displayed, and analyzed, by the program 110.

For image processing, the radiologist selects his/her preferred image processing parameters to be used by the program 110, which accentuate critical anatomic structures and potential pathology. In this particular case, the radiologist's clinical concerns focus on the lung fields, in the evaluation of potential malignancy and interstitial fibrosis (related to the medication therapy.

In determination of the image reconstructions, each individual radiologist has their own preferences for the best manner in which the imaging data is presented. Determination of optimal slice thickness is dependent upon the program 110 attributes, including acquisition parameters selected, corresponding noise levels, image processing techniques employed, and suspected pathology. The selection of the imaging planes utilized (e.g., axial, sagittal, coronal) and 2 vs. 3-dimensional reconstructions are also dependent upon individual preference, along with the modality, anatomy, and pathology.

The next step, image display, involves both presentations of the current imaging dataset, as well as historical imaging datasets, by the program 110. In this specific example, a prior chest CT reportedly contained a nonspecific 6 mm lung nodule. Image display must therefore, take into account optimal display of the prior key images, along with comparable display of the current images. This can be a trivial matter when the two imaging examinations were acquired using the same technology and acquisition protocols. In this particular example, however, the comparison CT was performed at an outside institution. As a result, the CT scanner 21 and protocol used for the outside CT exam were far different from that of the current study, which makes comparative display of current and prior images non-trivial. If the historical exam was performed using "conventional dose" acquisition parameters, while the current exam was perform using "low dose" acquisition parameters, differences exist in the optimal manner in image display.

A number of different forms of computerized decision support can be applied by the program 110, to assist the radiologist in analysis of the imaging dataset. One form of decision support is computer-aided detection (CAD) software, which is specifically designed to detect a specific type of pathology (e.g., lung nodule). The radiologist can elect to activate the CAD program, which in turn highlights suspected lung nodules.

Another computerized decision support application can analyze morphology and/or texture of the lung nodule, and provide probability statistics as to suspected clinical significance (i.e., probability of malignancy). It is important to understand that the relative performance of these computerized CAD programs 110 are dependent upon the acquisition parameters of the imaging dataset, which have been customized to minimize radiation dose at the pre-defined quality threshold (MQT). As a result, it is important that CAD program 110 selection be tailored to the acquisition parameters employed.

Another computerized decision support program involves automated volume and density measurement of the lung nodule. Once the lung nodule is identified on corresponding historical and current images, the computer program 110 can derive comparative volumetric and density measurements which are important to quantifying growth, tumor doubling time, and differential diagnosis. All of these decision support features must take into account technical differences between the two different datasets, in order to enhance the technical accuracy of the computer program-derived measures.

It is important to realize that diagnostic accuracy can be highly variable between different radiologists. This inter-radiologist variability is multi-factorial in nature and can be explained by differences in education, training, technology utilized, technical parameters in the imaging dataset, anatomy, and pathology. Studies have shown that radiologists who have increased experience and training in a specific sub-specialty area (e.g., thoracic radiology) are more adept at interpreting "suboptimal" or lesser quality imaging datasets than their non-subspecialty trained counterparts (e.g., general radiologists).

As a result, as acquisition parameters are modified to a greater degree (e.g., greater amount of dose reduction) by the program 110, the perceived image quality deteriorates and inter-radiologist variability in diagnostic accuracy and clinical performance may increase. This is an important ramification of the "professional" aspects of the RDQI. While the "technical" RDQI may be optimized by the program 110 to maximize radiation dose reduction at the minimal quality threshold (MQT), there is an untoward impact on "professional" performance, which in this case, equates to interpretation accuracy.

As previously mentioned, a number of technical resources can be utilized by the program 110 in step 318, to enhance radiologist performance (e.g., image processing, CAD), but it is still important that the RDQI program 110 accurately record, track, and analyze potential differences in radiologist performance, and utilize this data proactively to maximize clinical outcomes in step 319.

To illustrate how this inter-radiologist performance RDQI data can be used proactively by the program 110, four different radiologists are evaluated.

Dr A. is a general radiologist at Mercy Hospital, who works in the same department as Dr. B, a subspecialty trained thoracic radiologist. Drs. C and D are also general and thoracic radiologists respectively, who work at nearby Good Samaritan Hospital. In addition to training and institutional differences, the radiologists differ in their respective experience levels, with Radiologist A recently trained (2 years post-residency), radiologist C being 15 years post-residency, and radiologists B and D both being 10 years post residency. Mercy Hospital has been profitable and financially sound, resulting in a state of the art imaging department. Good Samaritan, on the other hand, has been losing money for years and as a result has a somewhat antiquated imaging department. These radiologist profiles can be summarized as follows:

Radiologist A: General radiologist, lesser experience, superior technology.

Radiologist B: Thoracic radiologist, moderate experience, superior technology.

Radiologist C: General radiologist, extensive experience, poor technology.

Radiologist D: Thoracic radiologist, moderate experience, poor technology.

Included in the RDQI database 114 are diagnostic accuracy scores for radiologists, which characterize interpretation accuracy as it relates to differences in the modality, anatomy, pathology, and RDQI. As subspecialty trained thoracic radiologists with comparable experience, Radiologists B and D have higher interpretation accuracy scores for chest CT in the evaluation of lung cancer, than their general radiologist counterparts (Radiologists A and C). Radiologists B and D do exhibit minor differences with one another in accordance with the sophistication of technology employed by their respective imaging departments, with Radiologist B having slightly higher interpretation accuracy scores than Radiologist D. When comparing Radiologists A and C, almost identical interpretation accuracy scores are noted, where technology and experience differences offset one another.

The extent of inter-radiologist variability is accentuated as the RDQI measures are magnified. As lower radiation dose exposures are utilized for a given CT exam, the differences in interpretation accuracy become magnified, so that subspecialty training and technology differences become accentuated. As a result, the interpretation accuracy scores of Radiologists A and C become more adversely affected.

By the program 110 utilizing this data prospectively, the determination of the optimal CT protocol can be adjusted by the program 110 in accordance with the radiologist assigned to interpret a given CT exam. In this example, the CT technologist working at Mercy Hospital may select a different MQT for Dr. A, as opposed to Dr. B. While the technology utilized, exam type, and clinical indication are the same, the differences in radiologist performance would dictate that Radiologist A have a higher MQT than Radiologist B (in order to maintain the same level of diagnostic accuracy). The resulting RDQI would reflect this difference, with the CT radiation dose lower for Radiologist C than Radiologist A.

This potential interaction effect between "technical" and "professional" RDQI data has important ramifications, as it relates to selection of a service provider and allocation of services. A patient, referring clinician, or third party payer could potentially utilize this RDQI data to provide an informed choice in selecting the optimal imaging provider, on an institutional departmental, and/or individual staff levels. At the same time, decision support technologies can be developed to target specific provider deficiencies, with the longitudinal RDQI data serving as an objective means to assess technology performance and clinical outcomes.

Another important step in the overall process and analysis of RDQI is administrative oversight, which is important in ensuring that departmental performance standards are being maintained (relative to technology and staff performance), that there is ongoing education and training efforts aimed at improving deficiencies, and there is compliance with industry and governmental regulations. The various administrative analyses which can be performed using the RDQI program 110, in step 320, include:

1) Mean Radiation Dose According to Exam Type
   a) Technology
   b) Technologist
   c) Radiologist
   d) Clinician
   e) Patient
2) Mean Quality Scores According to Exam Type
   a) Quantitative analysis
   b) Comprehensive exam quality score
   c) Individual component quality scores
   d) Qualitative analysis
   e) Comprehensive exam quality scores
      i) Technologist
      ii) Radiologist
      iii) Clinician
      iv) Technology
      v) Patient
3) Mean MQT Scores
   a) Technology
   b) Technologist
   c) Radiologist
   d) Clinician
   e) Patient As stated above, the administrative analyses can be performed and tracked by the program 110 in step 320 according to modality, anatomy, clinical indication, and technology utilized.

As an example, an administrator may want to ascertain how screening mammography examinations in his/her institution compare with national statistics, when it comes to mean radiation dose. The first variable to consider in this comparative analysis is the different types of technology being utilized within the imaging department. The administrator may query the national RDQI database 114 to have the program 110 compare institutional and national mean radiation dose values for institutions using the same type of mammography acquisition device.

Upon reviewing this data, for example, the administrator learns that mean radiation dose in his/her imaging department is 10% higher than national averages, for those institutions using similar technology. In order to find out whether this difference is due to differences in the patient population being served, the administrator queries the database 114 for the program 110 to compare his/her institutional statistics with national statistics of institutions using the same technology and with comparable patient profile scores. Note that the patient profile takes into account a number of demographic and clinical variables, including but not limited to socioeconomic status, body habitus, education, compliance, and overall health status. In the case of mammography, an additional factor within the patient profile is average breast density, which is unique to mammography and impacts radiation dose requirements.

Upon performing this analysis, the administrator learns that his/her institution has 11% higher mean exam radiation dose, for example, when compared to national peer reference values. Having already factored in technology and patient profile into the analysis, the administrator is concerned that the relatively higher mean exam radiation dose may be due to inadequate staff performance at the level of the technologist. The administrator generates a query for the program 110 to evaluate the mean exam radiation dose for each individual technologist performing mammography within his/her institution. This analysis by the program 110 demonstrates a high degree of inter-technologist variability, with some technologists averaging 2x the radiation dose of other technologists. When comparing these "high dose" technologists with the "low dose" technologists, a few interesting observations are made:

1) "High dose" technologists perform far less number of mammography exams on average than their "low dose" counterparts.
2) "High dose" technologists have less experience in mammography (in terms of the number of years doing mammography).
3) "High dose" technologists have less education (as determined by the average number of dedicated mammography continuing medical education (CME) credits per year) than "low dose" technologists.
4) No significant differences exist in mean quality scores for the two groups of technologists.

The administrator concludes that a contributing factor to his/her institution's higher than expected mean radiation dose for mammography is due to inter-technologist variability, which in turn is in part due to differences in education/training and experience. The administrator elects to institute the following interventions, in an attempt to reduce mean radiation dose on both departmental and individual staff levels:

1) Create technologist scheduling requirements calling for all mammography technologists to perform a minimum number of annual exams.
2) Institute mandatory mammography in-services for all staff, aimed at improving radiation dose reduction and image quality.
3) Create a mentoring system where "high dose" technologists can shadow "low dose" technologists for a defined period of time.
4) Have monthly reviews of radiation dose and quality statistics of all mammography technologists, performed by a supervisory technologist.

After institution of these programs, a six month follow-up analysis demonstrated interval improvement at both a departmental and individual staff level with almost no demonstrative inter-technologist difference in mean radiation dose per mammography exam. When compared with national peer reference data, however, a 4% difference remained which could not be accounted for by technologist performance. When using the program 110 to query the database 114 for mean radiation dose per exam as a function of each radiologist, the administrator learned that one radiologist was an outlier to his/her peers within the department. This one radiologist's mean radiation dose was 30% higher than the other radiologists, which upon further review was due to his/her insistence on maintaining a higher MQT than his/her peers. When this particular radiologist was questioned, he/she believed that overall image quality at the lower dose acquisitions was insufficient. The chief radiologist elected to remove this radiologist from the mammography rotation, and subsequent analyses of mean radiation dose per mammography exam fell in line with national reference data.

This example illustrates how an analysis of the RDQI database 114 by the program 110 could be used to improve technical and professional by identifying limiting factors. Similar analyses could be performed by the program 110 on quality and MQT components of the RDQI database 114, in an attempt to optimize radiation safety and quality. The standardization of this data provides a reliable means to analyze service providers on local, regional, national, and international levels. At the same time, this data can be used to facilitate research, education and training, technology development and refinement, and creation of objective best practice clinical standards (i.e., EBM guidelines)

In addition to administrative analysis, the RDQI can also play a major role in comparative technology assessment. In the screening mammography example, one can see how different mammography acquisition devices 21 can be objectively compared to determine relative performance. In the field of digital mammography, one of the most important technology differentiators is the specific type of detector used by different manufacturers. In order to objectively assess technology performance, one could effectively use the program 110 to compare different technology providers, after accounting for institutional, staff, and patient differences. One could use the program 110 to quantitatively compare mean exam radiation dose, mean quality, and MQT scores. A prospective customer could make an informed and educated decision as to the most cost effective technology to purchase, after review by the program 110 and factoring in its own institutional, patient, and staff variables. At the same time, a digital mammography vendor who replaces its detector technology can utilize the program 110 to accurately compare radiation and quality data of its customers, to determine the net effect the new and old detector technologies had on technical and clinical performance.

Up to this point in time, the RDQI database 114 and subsequent analyses have focused on the diagnostic aspect of medical imaging and ionizing radiation. In reality, ionizing radiation is also used for therapeutic purposes, most commonly in the treatment of cancer (i.e., radiation oncology). The same principles of the RDQI can also be applied to the field of radiation oncology, as an objective means for the program 110 to record, track, and analyze technical and clinical parameters related to radiation dose, patient safety, and clinical outcomes. The specific data which would be recorded by the program 110 in the "therapeutic" RDQI database 114 include:
1) Tumor Characterization
   a) Specific type and tissue of origin
   b) Tumor stage (TNM classification)
   c) Pathology grade
   d) Genetic profile
   e) Volumetric measurements
2) Radiation Treatment
   a) Fractional and collective radiation dose administered
   b) Target tissue and affected non-target tissue
   c) Radiation delivery mode
   d) Pre-existing radiation history (diagnostic, therapeutic, and environmental)
   e) Mode of radiation delivery
   f) Technologies utilized
3) Clinical Response
   a) Reduction in tumor volume
   b) Change in tumor markers
   c) Cessation of clinical signs and symptoms
   d) Duration of tumor absence
   e) Change in tumor size over time
4) Complications
   a) Local tumor recurrence
   b) Radiation-induced iatrogenic complications
   c) Radiation side effects
   d) Radiation carcinogenesis
5) Additional Treatment
   a) Adjuvant chemotherapy
   b) Steroids
   c) Surgery
   d) Other Medications This therapeutic RDQI database 114 provides an objective way to assess technology and individual stakeholder performance in the radiation therapy; taking into account a number of clinical and technical variables such as tumor type, patient profile, tumor stage, genetic composition, treatment regimen, iatrogenic complications, and technology utilized. The clinical outcomes can be determined by the program 110, by reduction in tumor volume, decrease in tumor markers, improvement in clinical signs and symptoms, lack of tumor recurrence, and radiation-related complications.

There are at least three components of the invention, all of which are contained within the RDQI database 114. The first is the "Technical" component, which defines an objective and quantifiable relationship between radiation safety (as determined by radiation dose) and image quality. This technical measure of the RDQI is determined by the program 110 by a number of variables including the various technologies utilized in image acquisition and processing, and the various stakeholders who are involved in the delivery of medical imaging services. These stakeholders and their respective responsibilities in the imaging chain would include the following:

1) Medical physicist: responsible for assessing equipment performance and calibration, compliance with regulatory standards (related to radiation safety), and establishment of departmental protocols related to radiation safety.
2) Technologist: responsible for image acquisition and processing, adherence to departmental protocols, patient safety and comfort, and documentation of adverse actions.
3) Radiologist: responsible for ensuring patient safety, overall image quality, compliance with industry-wide standards, creation of imaging protocols, technology selection, treatment of adverse actions, establishment of appropriateness criteria for imaging exams and clinician consultations.
4) Clinician: responsible for appropriate exam selection and ordering, preventative screening, overall patient safety, treatment of complications, input of clinical data relevant to imaging diagnosis and triage.
5) Administrator: responsible for compliance with institutional guidelines, technology and staff performance evaluation, documentation of adverse actions, staff education, training, and credentialing, and customer satisfaction.
6) QA specialist: responsible for establishing policy and procedures related to image quality assessment, staff education and training, image quality oversight and intervention.

The individual assessment of staff performance relative to these responsibilities can be incorporated by the program 110 into the RDQI analysis, in addition to comprehensive RDQI metrics which are listed above.

The data which is recorded, tracked, and analyzed by the program 110 within the various RDQI databases 114 provides an objective measure of radiation safety and quality for any given imaging service provider. By the program 110 standardizing the data recorded, the program 110 can combine RDQI databases 114 from multiple institutions for meta-analysis. This provides an objective tool for comparative assessment of individual stakeholder groups, technologies, and institutional providers. At the same time, this multi-institutional meta-analysis provides an effective tool for the establishment of "best practice" guidelines, evidence-based medicine standards, and expectations for technology performance.

Since recorded RDQI data is specific to the individual exam type, modality, clinical indication, and patient, customized metrics can be created by the program 110 taking into account these variables. This creates a mechanism where radiation and quality measures can be customized by the program 110 in accordance with the unique attributes of each patient and the clinical circumstances prompting the medical imaging procedure (i.e., patient and context-specific analyses, related to radiation safety and image quality).

The data derived from the RDQI analytics can be used by the program 110 for decision support at the point of care, so that any given stakeholder can access context-specific and patient-specific reference data to assist the task at hand.

As an example, a technologist performing an abdominal CT exam to re-evaluate a documented liver mass can input a series of data from the RDQI database 114, in order for the program 110 to determine the optimal exam protocol, acquisition parameters, and image processing; and in order to achieve a balance between radiation safety and image quality specific to that individual patient and clinical context. Data specific to the technology being utilized (e.g., CT scanner 21), clinical indication (e.g., liver mass), and individual patient (e.g., body habitus, cumulative radiation dose) can be used by the program 110 to search the multi-institutional RDQI databases 114 to identify optimal exposure parameters and the imaging protocol which will achieve the desired level of radiation safety and image quality.

The second component of the invention is the "Professional" RDQI analysis, which correlates radiation safety, image quality, and interpretation accuracy data. This multivariate analysis would take into account many of the same data previously described (e.g., clinical indication, patient profile, exam type, technology being utilized), for the program 110 to create an objective measure of diagnostic accuracy (relating to radiation dose and image quality). In this analysis, the specific stakeholder being evaluated will be the radiologist or clinician tasked with primary interpretation of the medical imaging dataset.

This "professional" component of the RDQI analysis, uses the program 110 to analyze inter-radiologist performance variability for a given "technical" RDQI. In this example, three different physicians (general radiologist, pulmonologist, and thoracic radiologist) are reviewed, and their respective performances assessed by the program 110 for a given set of low dose chest radiographs (which have been "technically" optimized for achieving the lowest possible radiation dose for a pre-determined minimum quality threshold).

Because professional performance is dependent upon an individual stockholder's education, training, and experience, one would expect some degree of variability between them. The thoracic radiologist who has subspecialty training in chest imaging would in all likelihood have higher interpretation accuracy than his lesser trained general radiologist and pulmonologist counterparts. The disparity between them would in all likelihood be magnified by variables adversely affecting image quality (e.g., patient obesity, portable positioning, and lesser quality acquisition technologies).

These professional RDQI program 110 analyses can be used to assist prospective customers in service provider selection (at both an institutional and individual staff member level) and in the optimization of imaging protocols. With knowledge of the physician tasked with interpretation, a technologist can modify the exam protocol and acquisition parameters in accordance with the professional profile of the reader. In this manner, the RDQI program 110 provides decision support for the technologist as to the most effective means to optimize the "technical" and "professional" RDQI data. Using the example of the three different readers (general radiologist, pulmonologist, and thoracic radiologist), the technologist performing the exam will have the program 110 customize the acquisition protocol in accordance with the reader profile. Depending upon the reader, the technologist will select those acquisition parameters which achieve the desired radiation dose/quality index and the desired level of interpretation accuracy. As a result, the thoracic radiologist may use the program 110 to render the desired level of interpretation accuracy at a lower radiation dose then the pulmonologist or general radiologist. Using the professional RDQI databases 114, the technologist could insert the identity of the reader, and the computer program 110 can in turn, derive the minimal quality threshold (MQT), for that given exam type, patient, and clinical indication.

The third component of the RDQI database 114 is the "Therapeutic" RDQI analysis, which defines the relationship between radiation dose and quality relating to therapeutic applications of radiology (e.g., radiation oncology). The "therapeutic" RDQI program 110 correlates the radiation dose with measures of clinical quality, which can be defined by therapeutic outcomes (e.g., decrease in tumor volume, cessation in clinical symptoms, and lack of tumor recurrence).

As is the case with the "technical" and "professional" RDQI measures, the "therapeutic" RDQI is also dependent upon a number of technology, patient, and context-specific variables. These would include anatomy (i.e., organ type), location (i.e., proximity to critical structures), pathology (i.e., tumor type and grade), tumor markers (i.e., genetic composition), technology employed, and therapeutic regimen (i.e., individual and collective radiation dose delivered over time). The goal of optimizing the "therapeutic" RDQI, is to achieve the highest level of quality for the lowest radiation dose. This would be dependent upon the radio-sensitivity of the tumor, along with the other variables previously listed.

As tumor genetics (i.e., molecular composition) are better recorded and analyzed in general, the RDQI program 110 will provide an effective means to combine multi-institutional RDQI databases 114 in order to determine optimal treatment protocols for each individual patient and tumor type. In addition to providing a data-driven mechanism to predict tumor response to the proposed radiation therapy regimen, the RDQI program 110 can also predict iatrogenic complications related to the patient profile, tumor location, and technology being utilized. The prediction of radiation induced iatrogenic complications (as well as therapeutic response) is dependent upon multiple clinical and technical factors including each individual patient's radiation and medical histories, the technology employed, radiation treatment planning, and stakeholder performance (e.g., radiation oncologist).

As is the case with the "technical" and "professional" RDQI analytics, the "therapeutic" RDQI program 110 can be used to determine best clinical practice guidelines, technology selection, and relative performance differentiation of different service providers.

The same principles of the "therapeutic" RDQI program 110 can also be applied to medical oncology, where the pharmaceutical dose of chemotherapeutic agents is correlated with clinical quality metrics. The general premise remains the same—optimizing dose and quality can be accomplished through rigorous data collection and analysis by the program 110.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A computer-implemented method for measuring radiation dose exposure and image quality in an imaging examination on a patient, comprising:
    retrieving patient information from a database, and displaying said patient information on a display;
    compiling radiation iatrogenic risks to the patient using a processor;
    utilizing decision support to obtain comparative data from said database to determine examination selection, said decision support including retrieving from said database and displaying on said display, additional information regarding report findings and radiation data attributable to prior imaging studies;
    deriving radiation dose exposure and carcinogenesis risk to the patient utilizing said decision support additional information, using said processor;
    deriving estimated radiation dose exposure to the patient for the imaging examination, including patient-specific data, using said processor;
    receiving an inputted selection of an imaging examination based upon said derivation of estimated radiation dose exposure;
    creating an optimal imaging examination protocol of said imaging examination to maximize radiation dose reduction, image quality and diagnostic accuracy, using said processor; and
    displaying said optimal imaging examination protocol on said display, based upon a derived host institution technology, staffing, and performance data, using said processor;
    wherein said optimal imaging examination protocol includes acquiring a test image using standard/default acquisition parameters, introducing noise into said test image, determining a minimum quality threshold (MQT) of image quality, calculating acquisition parameters for the imaging examination, performing the imaging examination, and determining an examination specific radiation dose quality index.

2. The method of claim 1, further comprising:
    inputting the patient's biometrics, using a biometrics system, into said database to retrieve said patient information.

3. The method of claim 1, wherein said patient information includes prior clinical, laboratory, and imaging examination data on the patient.

4. The method of claim 3, wherein said imaging examination data includes a series of examinations and patient-specific data related to individual examination radiation dose, cumulative radiation dose, and radiation iatrogenic risk.

5. The method of claim 4, wherein compiling said radiation iatrogenic risks further comprises:
    performing analytics on a carcinogenesis risk associated with prior imaging studies, estimated environmental radiation exposures, and deterioration risk to the patient from radiation, using said processor.

6. The method of claim 5, wherein said decision support further comprises:
    inputting clinical data into said database, said clinical data including clinical indication, past medical/surgical history, current medical problems, ongoing treatment, historical imaging studies, patient profile, imaging examination type and positioning, anatomic region, radiologist and clinician profiles, and supporting technologies.

7. The method of claim 6, wherein said database is an outside institutional database, and said additional information is exported electronically to an in-house database.

8. The method of claim 6, wherein deriving said radiation dose exposure further comprises:
    deriving, using said processor, individual examination radiation dose exposures, cumulative patient radiation dose exposures, estimated environmental radiation dose exposures, radiation-induced carcinogenesis risk, cumulative carcinogenesis risk, and additional radiation risk.

9. The method of claim 8, wherein deriving said radiation dose exposure further comprises:
    deriving, using said processor, estimated radiation dose exposures, estimated cost estimates, comparative clinical value, options for radiation dose reduction, options for enhancing clinical value, options for minimizing cost, and comprehensive cost-benefit analysis.

10. The method of claim 9, wherein deriving estimated radiation dose exposure to the patient, using said processor, includes estimated radiation dose for conventional CT, estimated radiation dose for low dose CT, and estimated radiation dose for ultra-low dose CT.

11. The method of claim 10, wherein said optimal imaging examination protocol includes acquisition parameters, CT kernel, collimation, image processing, and noise reduction filters.

12. The method of claim 11, wherein said optimal imaging examination protocol further includes institutional-specific protocol optimization, regional protocol optimization, and multi-institutional protocol optimization.

13. The method of claim 11, further comprising:
electronically ordering and scheduling said imaging examination.

14. The method of claim 13, further comprising:
determining optimal acquisition parameters using a just-noticeable-difference (JND) metric protocol, using said processor, said JND metric protocol including:
acquiring said test image by one of using said standard/default acquisition parameters using said imaging device, or by measuring actual radiation exposure using a sensor;
introducing said noise as computer-derived noise into said test image using low dose acquisition parameters, using said processor;
progressively increasing said noise into said test image until a pre-determined minimum quality threshold (MQT) score is reached and equivalent to a predetermined JND, using said processor;
determining a perceptual and derived image quality, using said processor, for radiologist review and approval; and
calculating, using said processor, said acquisition parameters which will produce said desired image quality using said predetermined JND.

15. The method of claim 14, wherein said MQT score is determined by said processor, based upon clinical parameters, patient profile, imaging examination being performed, technology utilized, and individual radiologist profile.

16. The method of claim 14, further comprising:
dynamically adjusting imaging quality requirements of said acquisition parameters to produce said desired image quality during said imaging examination, using said processor.

17. The method of claim 14, wherein said predetermined JND is 1.5 JND.

18. The method of claim 14, further comprising:
repeating said calculating step at multiple levels within an anatomic region of interest during said imaging examination, to dynamically optimize said acquisition parameters, using said processor.

19. The method of claim 18, further comprising:
calculating a comprehensive examination radiation dose exposure of said imaging examination, using said processor; and
recording said comprehensive examination radiation dose exposure in said database.

20. The method of claim 19, further comprising:
comparing said calculated comprehensive examination radiation dose exposure of said imaging examination, with said derived estimated radiation dose exposure for the imaging examination based upon standard/default acquisition parameters, using said processor.

21. The method of claim 20, presenting data to an imaging provider and referring physician regarding said comparative analytics at a time of imaging examination order entry and said imaging examination protocol.

22. The method of claim 20, further comprising:
recording quality-centric metrics in said database, including at least one of anatomic coverage, positioning, collimation, contrast resolution, spatial resolution, density and measurement calibration, noise, image processing and reconstruction, artifacts, registration of disparate datasets, motion, contrast enhancement; and
pooling said quality-centric metrics to calculate a comprehensive quality score, using said processor.

23. The method of claim 20, further comprising:
comparatively analyzing derived radiation dose exposure and image quality by creating a mathematical ratio of image quality divided by radiation dose exposure, using said processor, so that a higher the value, a greater the efficiency of radiation dose exposure and image quality.

24. The method of claim 23, further comprising:
creating a standard metric of a quality per unit dose, as a quantitative measure of image quality divided by said radiation dose exposure.

25. The method of claim 20, further comprising:
calculating an exam-specific radiation dose quality index (RDQI) score, using said processor, which reflects a total examination radiation dose exposure and an objective measure of image quality, and recording said RDQI in said database.

26. The method of claim 25, further comprising:
applying specialized noise reduction filters and/or imaging processing algorithms to imaging dataset from said imaging examination, using said processor, to decrease noise and enhance contrast resolution.

27. The method of claim 26, further comprising:
applying computerized decision support to an analysis of said imaging dataset.

28. The method of claim 27, further comprising:
analyzing differences in user performance, and in RDQI scores to maximize clinical outcomes.

29. The method of claim 28, further comprising:
modifying said optimal imaging examination protocol and acquisition parameters, in accordance with a professional profile of said user, using said processor.

30. The method of claim 29, further comprising:
automatically identifying said optimal acquisition parameters as standard/default acquisition parameters to the technologist prior to said imaging examination.

31. The method of claim 28, further comprising:
performing administrative analyses, using said processor, including at least one of mean radiation dose according to imaging examination type, mean quality scores according to imaging examination type, qualitative analyses, comprehensive examination quality scores, and mean MQT scores, with respect to modality, anatomy, clinical indication and technology utilized.

32. The method of claim 31, further comprising:
tracking, analyzing and storing in said database, at least one of technical and clinical parameters related to radiation dose exposure, patient safety and clinical outcomes, said clinical parameters including tumor characterization, radiation treatment, clinical response, complications, and additional treatment, to assess performance in radiation therapy.

33. The method of claim 32, further comprising:
correlating, using the processor, said radiation dose exposure with measures of clinical quality, to define therapeutic outcomes.

34. The method of claim 32, further comprising:
combining RDQI scores in databases from multiple institutions, for meta-analysis, to provide a comparative assessment of individual stakeholder groups, technologies, and institutional providers, and establish best practices guidelines.

35. The method of claim 34, further comprising:
correlating said meta-analysis of institutional providers with reference peer groups to provide consumers with objective data, which are categorized in accordance with specific medical imaging examinations or patient profiles.

36. The method of claim 35, further comprising:
applying said meta-analysis to third party payers; and
displaying objective image quality and safety data for prospective or existing customers, such that individual payers' performance related to that of competitors, can be determined.

37. A non-transitory computer-readable medium which includes instructions for measuring radiation dose exposure and image quality in an imaging examination on a patient, comprising:
retrieving patient information from a database, and displaying said patient information on a display;
compiling radiation iatrogenic risks to the patient using a processor;
utilizing decision support to obtain comparative data from said database to determine examination selection, said decision support including retrieving from said database and displaying on said display, additional information regarding report findings and radiation data attributable to prior imaging studies;
deriving radiation dose exposure and carcinogenesis risk to the patient utilizing said decision support additional information, using said processor;
deriving estimated radiation dose exposure to the patient for the imaging examination, including patient-specific data, using said processor;
receiving an inputted selection of an imaging examination based upon said derivation of estimated radiation dose exposure;
creating an optimal imaging examination protocol of said imaging examination to maximize radiation dose reduction, image quality and diagnostic accuracy, using said processor; and
displaying said optimal imaging examination protocol on said display, based upon a derived host institution technology, staffing, and performance data, using said processor;
wherein said optimal imaging examination protocol includes acquiring a test image using standard/default acquisition parameters, introducing noise into said test image, determining a minimum quality threshold (MQT) of image quality, calculating acquisition parameters for the imaging examination, performing the imaging examination, and determining an examination specific radiation dose quality index.

38. A computer system which for measuring radiation dose exposure and image quality in an imaging examination on a patient, comprising:
at least one memory which contains at least one program comprising the steps of:
retrieving patient information from a database, and displaying said patient information on a display;
compiling radiation iatrogenic risks to the patient using a processor;
utilizing decision support to obtain comparative data from said database to determine examination selection, said decision support including retrieving from said database and displaying on said display, additional information regarding report findings and radiation data attributable to prior imaging studies;
deriving radiation dose exposure and carcinogenesis risk to the patient utilizing said decision support additional information, using said processor;
deriving estimated radiation dose exposure to the patient for the imaging examination, including patient-specific data, using said processor;
receiving an inputted selection of an imaging examination based upon said derivation of estimated radiation dose exposure;
creating an optimal imaging examination protocol of said imaging examination to maximize radiation dose reduction, image quality and diagnostic accuracy, using said processor; and
displaying said optimal imaging examination protocol on said display, based upon a derived host institution technology, staffing, and performance data, using said processor; and
wherein said optimal imaging examination protocol includes acquiring a test image using standard/default acquisition parameters, introducing noise into said test image, determining a minimum quality threshold (MQT) of image quality, calculating acquisition parameters for the imaging examination, performing the imaging examination, and determining an examination specific radiation dose quality index; and
a processor which executes the program.

* * * * *